United States Patent
Schirmer et al.

(10) Patent No.: US 10,703,742 B2
(45) Date of Patent: Jul. 7, 2020

(54) METHOD FOR PRODUCING 5-HYDROXYALKYL-SUBSTITUTED 1-PHENYL-1,2,4-TRIAZOLE DERIVATIVES

(71) Applicant: BAYER PHARMA AKTIENGESELLSCHAFT, Berlin (DE)

(72) Inventors: Heiko Schirmer, Solingen (DE); Philipp Rubenbauer, Bensheim (DE); Hans-Christian Militzer, Odenthal (DE); Marie-Pierre Collin-Kröpelin, Wuppertal (DE); Frank Süßmeier, München (DE); Kersten Matthias Gericke, Wuppertal (DE); Thomas Neubauer, Wuppertal (DE); Chantal Fürstner, Mülheim/Ruhr (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 16/098,238

(22) PCT Filed: May 2, 2017

(86) PCT No.: PCT/EP2017/060367
§ 371 (c)(1),
(2) Date: Nov. 1, 2018

(87) PCT Pub. No.: WO2017/191104
PCT Pub. Date: Nov. 9, 2017

(65) Prior Publication Data
US 2019/0144431 A1    May 16, 2019

(30) Foreign Application Priority Data

| | | | |
|---|---|---|---|
| May 3, 2016 | (EP) | ................................. | 16168163 |
| May 3, 2016 | (EP) | ................................. | 16168165 |
| May 3, 2016 | (EP) | ................................. | 16168166 |
| May 3, 2016 | (EP) | ................................. | 16168169 |
| May 3, 2016 | (EP) | ................................. | 16168172 |
| Sep. 3, 2017 | (EP) | ................................. | 17160086 |

(51) Int. Cl.
C07D 403/06    (2006.01)
C07D 249/12    (2006.01)

(52) U.S. Cl.
CPC ......... C07D 403/06 (2013.01); C07D 249/12 (2013.01)

(58) Field of Classification Search
CPC ........................... C07D 403/06; C07D 249/12
USPC ..................................................... 548/263.2
See application file for complete search history.

(56) References Cited

FOREIGN PATENT DOCUMENTS

| WO | 2010/105770 | 9/2010 | |
|---|---|---|---|
| WO | 2011/104322 | 9/2011 | |
| WO | 2016/071212 | 5/2016 | |
| WO | WO-2016071212 A1 * | 5/2016 | ........... C07D 403/06 |

OTHER PUBLICATIONS

International Search Report for PCT/EP2017/060367, dated Jun. 14, 2017, 4 pages.
Halfbrodt, Citation of NMR Peaklist Data within Patent Applications; published in Research Disclosure, Database No. 605005, Published Sep. 2014, 5 pages.
Berge et al., "Pharmaceutical Salts", J. Pharm. Sci., Jan. 1977, vol. 66, No. 1, 1-19.

* cited by examiner

*Primary Examiner* — Matthew P Coughlin
*Assistant Examiner* — Sagar Patel
(74) *Attorney, Agent, or Firm* — McBee Moore & Vanik, IP, LLC

(57) ABSTRACT

The present application relates to a novel and improved process for preparing 5-(hydroxyalkyl)-1-phenyl-1,2,4-triazole derivatives of the formula (I)

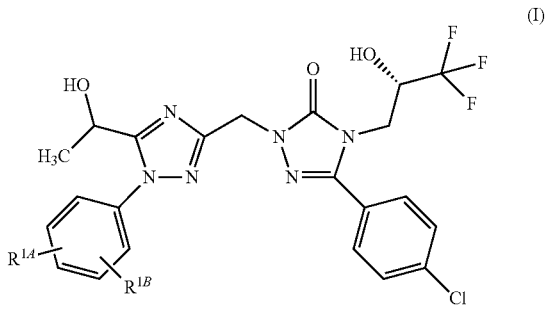

in which
$R^{1A}$ and $R^{1B}$ are independently selected from the group consisting of hydrogen, fluorine, chlorine, methyl, monofluoromethyl, difluoromethyl, trifluoromethyl, ethyl, methoxy, difluoromethoxy and trifluoromethoxy, to novel precursors for preparation thereof, and to the preparation and use of the crystalline polymorph I of (5-(4-chlorophenyl)-2-({1-(3-chlorophenyl)-5-[(1S)-1-hydroxy-ethyl]-1H-1,2,4-triazol-3-yl}methyl)-4-[(2S)-3,3,3-trifluoro-2-hydroxypropyl]-2,4-dihydro-3H-1,2,4-triazol-3-one of the formula (I-A-1).

10 Claims, 1 Drawing Sheet

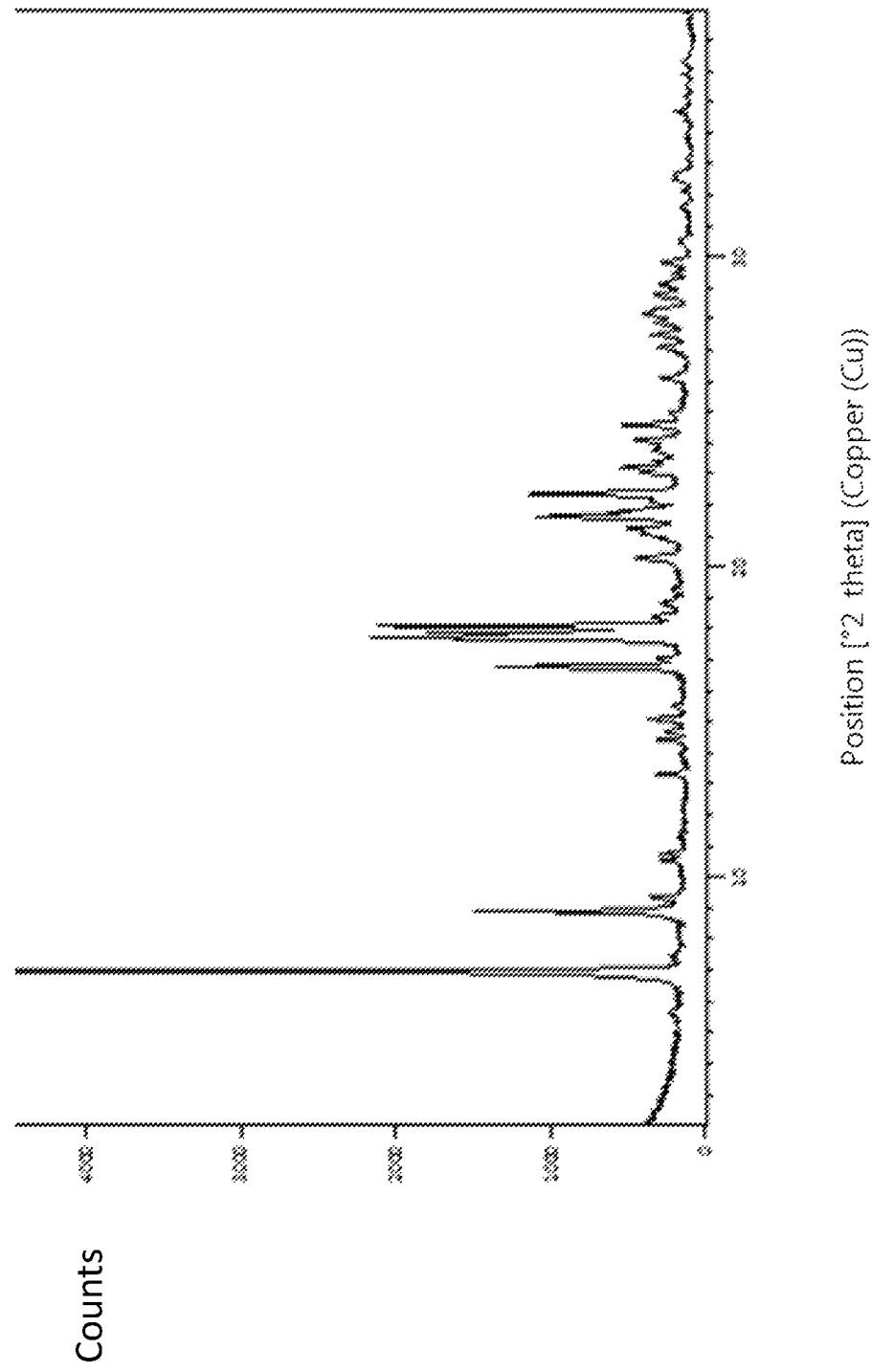

METHOD FOR PRODUCING 5-HYDROXYALKYL-SUBSTITUTED 1-PHENYL-1,2,4-TRIAZOLE DERIVATIVES

This application is the U.S. national phase of International Application No. PCT/EP2017/060367 filed 2 May 2017 which designated the U.S. and claims priority to EP Patent Application No. 16168163.0 filed 3 May 2016, EP Patent Application No. 16168165.5 filed 3 May 2016, EP Patent Application No. 16168169.7 filed 3 May 2016, EP Patent Application No. 16168166.3 filed 3 May 2016, EP Patent Application No. 16168172.1 filed 3 May 2016, and EP Patent Application No. 17160086.9 filed 9 Mar. 2017, the entire contents of each of which are hereby incorporated by reference.

The present application relates to a novel and improved process for preparing 5-(hydroxyalkyl)-1-phenyl-1,2,4-triazole derivatives of the formula (I)

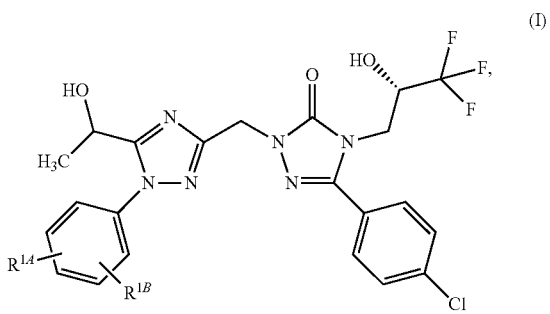

in which $R^{1A}$ and $R^{1B}$ are independently selected from the group consisting of hydrogen, fluorine, chlorine, methyl, monofluoromethyl, difluoromethyl, trifluoromethyl, ethyl, methoxy, difluoromethoxy and trifluoromethoxy, to novel precursors for preparation thereof, and to the preparation and use of the crystalline polymorph I of (5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one of the formula (I-A-1).

Compounds of the formula (I) act as potent dual V1a/V2 receptor antagonists and can be used as agents for prophylaxis and/or treatment of cardiovascular disorders and renal disorders, for example acute and (worsening) chronic heart failure, cardiorenal syndrome, hypervolaemic and euvolaemic hyponatraemia, liver cirrhosis, ascites, oedemas and the syndrome of inappropriate ADH secretion (SIADH), as disclosed in WO 2016/071212.

A general process for preparation of 5-phenyl-substituted 1,2,4-triazole derivatives is described in WO 2011/104322 (see Scheme 8, Examples 21, 25, 54, 56-61 and 68-70 therein). By means of the process described therein, however, it is not possible to achieve 1,3,5 substitution of the 1,2,4-triazole ring and especially 1-phenyl substitution of the 1,2,4-triazole ring in one process step.

Scheme 1 below shows the process for preparing the 5-phenyl-substituted 1,2,4-triazole derivatives according to WO 2011/104322.

Scheme 1: Synthesis of 1,2,4-triazole derivatives according to WO 2011/104322.

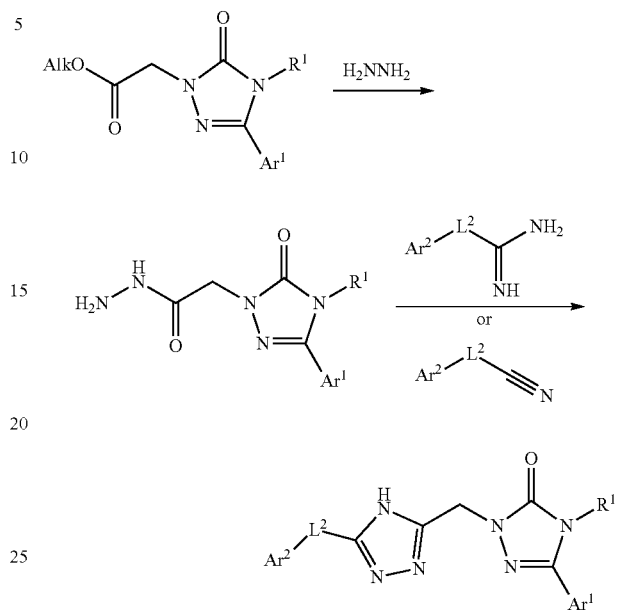

[WO 2011/104322: Scheme 8, page 32; $L^2$ = bond inter alia; $Ar^2$ = substituted phenyl inter alia; Alk = alkyl].

Compounds of the formula (I) and the preparation thereof are described in WO 2016/071212. The research synthesis described therein is regarded as the closest prior art. Proceeding from 5-(4-chlorophenyl)-4-[(2S)-3,3,3-trifluoro-2-hydroxypropyl]-2,4-dihydro-3H-1,2,4-triazol-3-one (II), the target compounds of the formula (I) are prepared in 4 stages with an overall yield of not more than ~12% of theory. The diastereomers of the formula (I-A) and (I-B) are obtained on the laboratory scale in a further stage from the diastereomer mixture (I) via a chiral diastereomer separation. The compounds of the formula (I) are obtained in solid form in WO 2016/071212, but there has been no description to date of a defined crystallization process of the end stage for preparation of a pharmaceutically usable crystal form.

Scheme 2 below shows the process for preparing the compounds of the formula (I).

Scheme 2: Synthesis of compounds of the formula (I) according to WO 2016/071212.

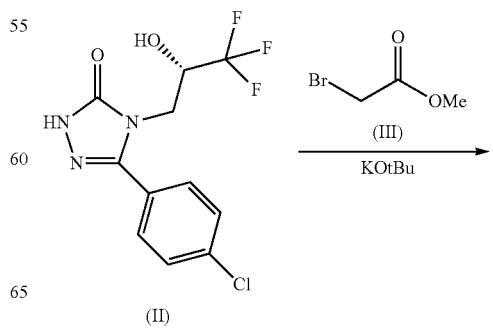

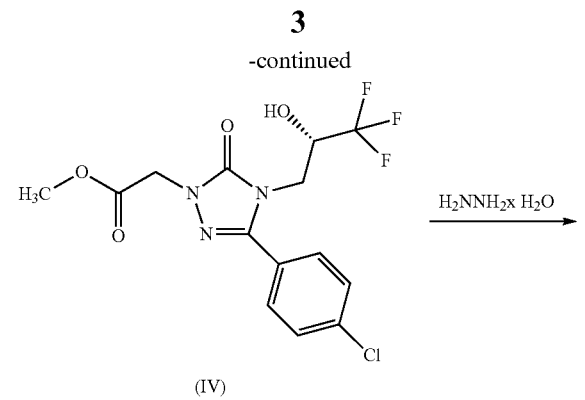

(IV)

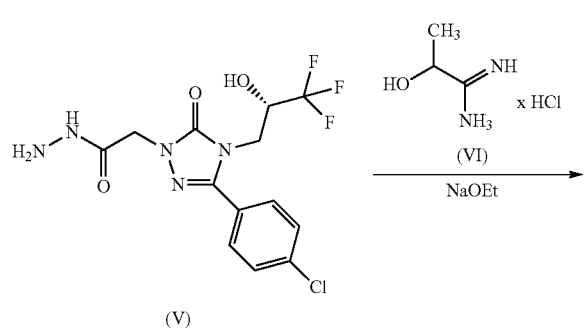

(V)

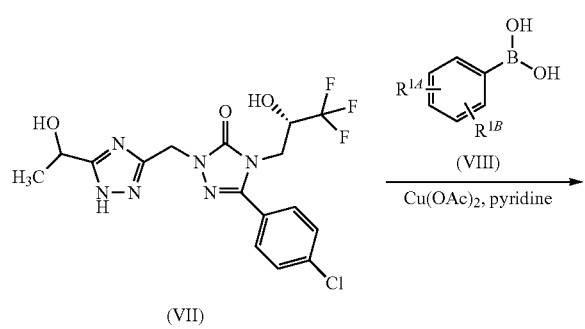

(VII)

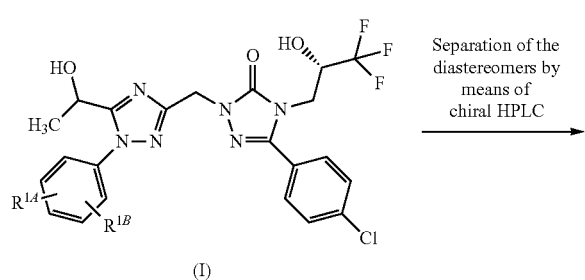

(I)

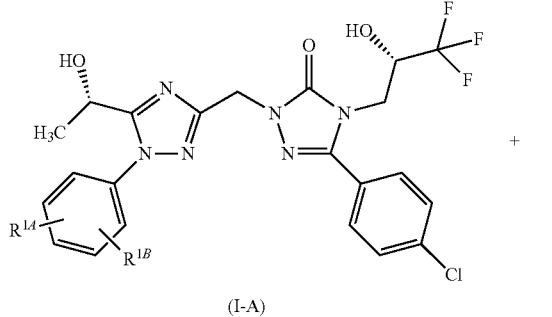

(I-A)

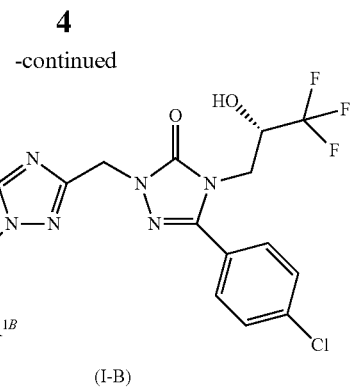

(I-B)

[$R^{1A}$, $R^{1B}$ = hydrogen, fluorine, chlorine, cyano, methyl, monofluoromethyl, difluoromethyl, trifluoromethyl, ethyl, methoxy, difluoromethoxy and trifluoromethoxy].

Up to and including step (V) to (VII), the synthesis disclosed in WO 2016/071212 is analogous to the process disclosed in WO 2011/104322.

For preparation of the compound of the formula (IV), 5-(4-chlorophenyl)-4-[(2S)-3,3,3-trifluoro-2-hydroxypropyl]-2,4-dihydro-3H-1,2,4-triazol-3-one (II) is reacted with methyl bromoacetate (III) to give methyl{3-(4-chlorophenyl)-5-oxo-4-[(2S)-3,3,3-trifluoro-2-hydroxypropyl]-4,5-dihydro-1H-1,2,4-triazol-1-yl}acetate (IV). Subsequently, (IV) is converted with hydrazine hydrate to 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (V). (V) is then reacted with the imide compound (VI) to give the mixture of the diastereomers 5-(4-chlorophenyl)-2-({5-[(1RS)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (VII). A copper-catalysed aryl coupling ("Chan-Lam coupling") of (VII) with a substituted phenylboronic acid (VIII) leads to the substituted 5-(1-hydroxyethyl)-1-aryl-1,2,4-triazole derivatives (I). Separation by chiral chromatography affords the individual diastereomers 5-(4-chlorophenyl)-2-({5-[(1S)-1-hydroxyethyl]-1-($R^{1A}$, $R^{1B}$)-phenyl-1H-1,2,4-triazol-3-yl}methyl)-4-[(2S)-3,3,3-trifluoro-2-hydroxypropyl]-2,4-dihydro-3H-1,2,4-triazol-3-one (I-A) and 5-(4-chlorophenyl)-2-({5-[(1R)-1-hydroxyethyl]-1-($R^{1A}$,$R^{1B}$)-phenyl-1H-1,2,4-triazol-3-yl}methyl)-4-[(2S)-3,3,3-trifluoro-2-hydroxypropyl]-2,4-dihydro-3H-1,2,4-triazol-3-one (I-B).

The reaction scheme outlined above is described in WO 2016/071212 as follows: The reaction sequence from a compound of the formula (II) via the compounds of the formulae (IV), (V) and (VII) to compounds of the formula (I) and the separation into the diastereomers (I-A) and (I-B); see Scheme 2 and Examples 1A, 2A, 4A and 10 to 83 therein.

However, this process which is known from WO 2016/071212 has various disadvantages in the reaction regime which have a particularly unfavourable effect in the preparation of the compounds of the formula (I) on the industrial scale. The overall yield over the four stages (II) to (I) is very low at less than 15% of theory (about 1.3% to 13.1%). Many steps proceed in very high dilution and with very high reagent excesses.

A particularly disadvantageous aspect of the synthesis described in WO 2016/071212 is found to be the synthesis steps (VII) to (I) (copper-mediated aryl coupling, "Chan-Lam coupling"), which proceeds only with a maximum isolated yield of 30% (between 3.0% and 30.1%) and is thus disadvantageous from an atom economy point of view. Another disadvantage is that the reaction can give rise to regioisomeric phenyltriazole derivatives via a coupling reaction to another ring nitrogen atom (ring tautomerism of the 1,2,4-triazole derivatives (VII)). This likewise has an adverse effect on the yield in this step; in addition, the regioisomeric products then have to be removed in a complex manner in an additional purification step. Furthermore, this reaction step is particularly disadvantageous for a synthesis on the industrial scale, since stoichiometric amounts of copper acetate are used in this reaction. This is disadvantageous since the remaining amounts of copper salt have to be removed down to below the maximum limit permissible in the product for regulatory reasons, which means additional cost and inconvenience. Moreover, the reagents should be obtainable in a simple and inexpensive manner.

In the synthesis according to WO 2016/071212, the stereoisomeric mixture of the formula (I) was separated into the diastereomers on the laboratory scale by means of chiral chromatography. Such a chromatographic separation is very costly and time-consuming and therefore disadvantageous for a synthesis on the industrial scale. Furthermore, this additional stage further reduces the overall yield. A further disadvantage is that the target compound, by the method described in WO 2016/071212, is not obtained in a pharmaceutically usable defined crystal form.

There was therefore a need for a synthesis practicable on the industrial scale that affords the compounds of the formula (I) reproducibly in a high overall yield, with low production costs and high purity. There was additionally a need for a synthesis which is practicable on the industrial scale and meets all regulatory demands that are to be complied with for use of the active ingredient in clinical trials and can be used for later regulatory submission.

Surprisingly, a very efficient process for preparation of the compound of the formula (I) has now been found, which meets the demands mentioned above. The novel process enables an efficient synthesis of 5-hydroxyalkyl-substituted 1-phenyl-1,2,4-triazole derivatives.

An important advantage of the process according to the invention is the distinct increase in yield over all stages. The novel process according to the invention as per process variant (A) affords the target compounds (I) in four stages in an overall yield of more than 20% of theory (between 23.8% and 53.2%). Chromatographic purification of intermediates is unnecessary. Thus, the final two stages in an alternative process variant (B) and even the final three stages in a further alternative process variant (C) can be conducted as a one-pot method. In this way, it is possible to achieve a further increase in the overall yield over four stages (up to 63.2%).

The schemes and process steps which are described hereinafter are synthesis routes to the inventive compounds of the general formula (I) and should not be regarded as a restriction. The person skilled in the art will be aware that the sequence of transformations as shown by way of example in Schemes 3 and 4 can be modified in various ways, and the sequence presented should therefore not be regarded as a restriction. In addition, it is possible to convert functional groups of individual radicals and substituents, especially those listed under $R^1$ and $R^2$, before and/or after the transformations described by way of example, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulphonamides, ester cleavage and hydrolysis, and the introduction and removal of temporary protecting groups or other reactions known to those skilled in the art. These conversions also include those wherein a functionality is introduced, which enables further conversion of substituents. Suitable protecting groups and reagents and reaction conditions for the introduction and detachment thereof are known to those skilled in the art (see, for example, T. W. Greene and P. G. M. Wuts; "*Protective Groups in Organic Synthesis*", 3rd Edition, Wiley 1999). Specific examples are cited in the text passages which follow.

Scheme 3 below illustrates the novel process according to the invention for preparing the compounds of the formula (I).

Scheme 3: Process according to the invention for preparing the compound of the formula (I).

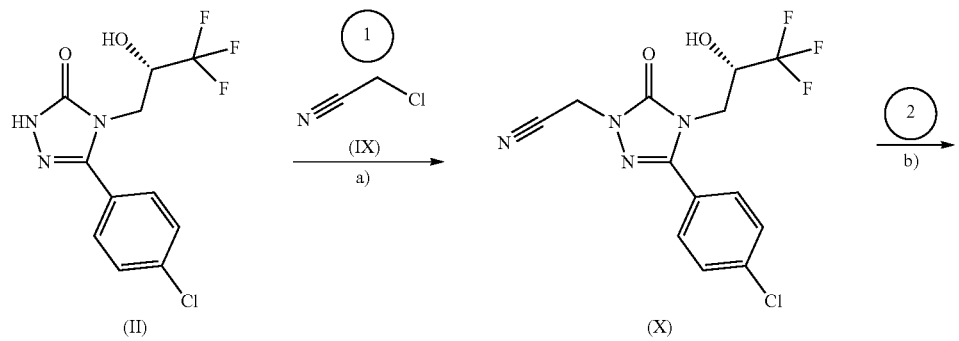

-continued

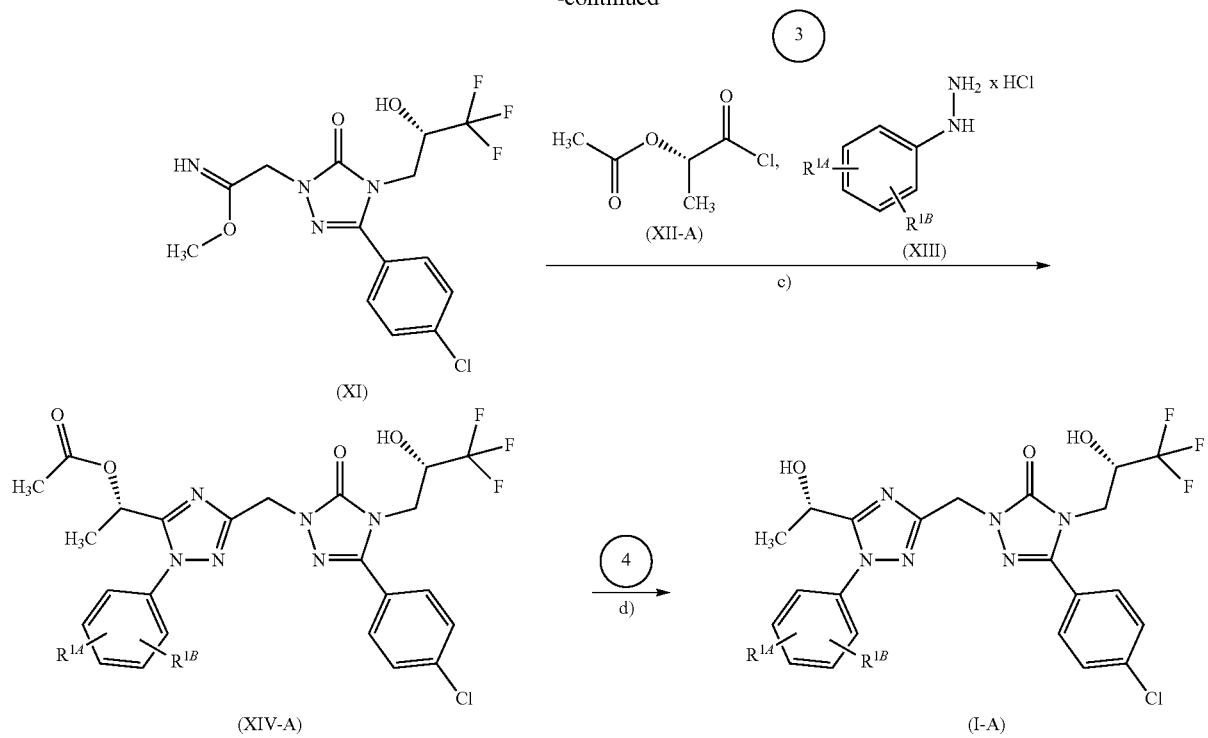

(XI)
(XII-A)
(XIII)
(XIV-A)
(I-A)

[R$^{1A}$, R$^{1B}$ = hydrogen, fluorine, chlorine, methyl, monofluoromethyl, difluoromethyl, trifluoromethyl, ethyl, methoxy, difluoromethoxy and trifluoromethoxy; a) Na$_2$CO$_3$, methyl isobutyl ketone; b) sodium methoxide, MeOH, c) 1. (XII-A), DIPEA, toluene/THF, 2. (XIII), DIPEA, THF; d) NaOH, MeOH].

Where, in the compounds of Synthesis Scheme 3,
R$^{1A}$ and R$^{1B}$ are independently selected from the group consisting of hydrogen, fluorine, chlorine, methyl, monofluoromethyl, difluoromethyl, trifluoromethyl, ethyl, methoxy, difluoromethoxy and trifluoromethoxy.

Where, preferably, in the compounds of Synthesis Scheme 3,
R$^{1A}$ and R$^{1B}$ are independently selected from the group consisting of hydrogen, fluorine and chlorine, where at least one of the substituents is not hydrogen.

Where, more preferably, in the compounds of Synthesis Scheme 3,
R$^{1A}$ is hydrogen, and
R$^{1B}$ is chlorine in the 2 position or in the 3 position.

Where, most preferably, in the compounds of Synthesis Scheme 3,
R$^{1A}$ is hydrogen, and
R$^{1B}$ is chlorine in the 3 position.

There follows a discussion of the individual stages of the process according to the invention for preparing the compound of the formula (I) according to Scheme 3. There is likewise discussion of alternatives which are characterized by the non-isolation of the compounds of the formula (XI) and (XIV).

For preparation of 5-(1-hydroxyethyl)-1-aryl-1,2,4-triazole derivatives (I), 5-(4-chlorophenyl)-4-((2S)-3,3,3-trifluoro-2-hydroxypropyl)-2,4-dihydro-3H-1,2,4-triazol-3-one (II) is converted to {3-(4-chlorophenyl)-5-oxo-4-[(2S)-3,3,3-trifluoro-2-hydroxypropyl]-4,5-dihydro-1H-1,2,4-triazol-1-yl}acetonitrile (X) (Step 1). Subsequently, the nitrile compound (X) is converted by reaction with sodium methoxide to methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) (Step 2). The 1,2,4-triazole ring is then formed via a three-component cyclization reaction, wherein the imino ester compound (XI) reacts with 2-acetoxypropionyl chloride (XII) and a substituted phenylhydrazine compound (XIII), and the 1-{3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[(R$^{1A}$,R$^{1B}$)-phenyl]-1H-1,2,4-triazol-5-yl}ethyl acetate (XIV) is obtained (Step 3). The subsequent detachment of the acetyl group affords the target compounds of the formula (I) (Step 4). In one variant (B), the process can be conducted in such a way that the protected acetate (XIV) is not isolated, but directly converted further in solution (Steps 3+4). In a further variant (C), the process can be conducted as a one-pot method via the stages (X)→(XI)→(XIV)→(I) (Steps 2+3+4); in this case, the overall process consists only of 2 isolated stages rather than 4 stages in the prior art.

An especially advantageous feature is the three-component cyclization reaction according to the invention for formation of the 1,2,4-triazole ring (Step 3), which enables introduction of the two ring substituents in the 1 and 5 positions in one process step, such that a high yield is achieved for this step (37.0% to 83.0% for Step 3; after protecting group attachment: 36.7% to 82.2% over 2 stages for Steps 3+4). The synthesis described in the prior art (Scheme 2) gives a significantly lower yield over two stages of 2.9% to 28.9% via the analogous sequence (V)→(VII)→(I).

A further advantageous feature is also the robustness of the process according to the invention, such that, as described above, the sequence can also be executed as a one-pot method (process variants B and C), such that the intermediates need not be isolated and, rather than being purified by chromatography, the intermediates are subjected directly to a subsequent step in the same reaction vessel and/or reaction medium. Such a one-pot method is especially advantageous for an industrial scale synthesis, since it is possible in this way to avoid additional workup steps, and a high overall yield for the process is achieved.

The starting compound of the formula (II) described in Synthesis Scheme 3 can be prepared according to Synthesis Scheme 4 below, proceeding from starting compounds that are commercially available or known to the person skilled in the art:

Scheme 4: Process for preparing the compounds of the formula (II)

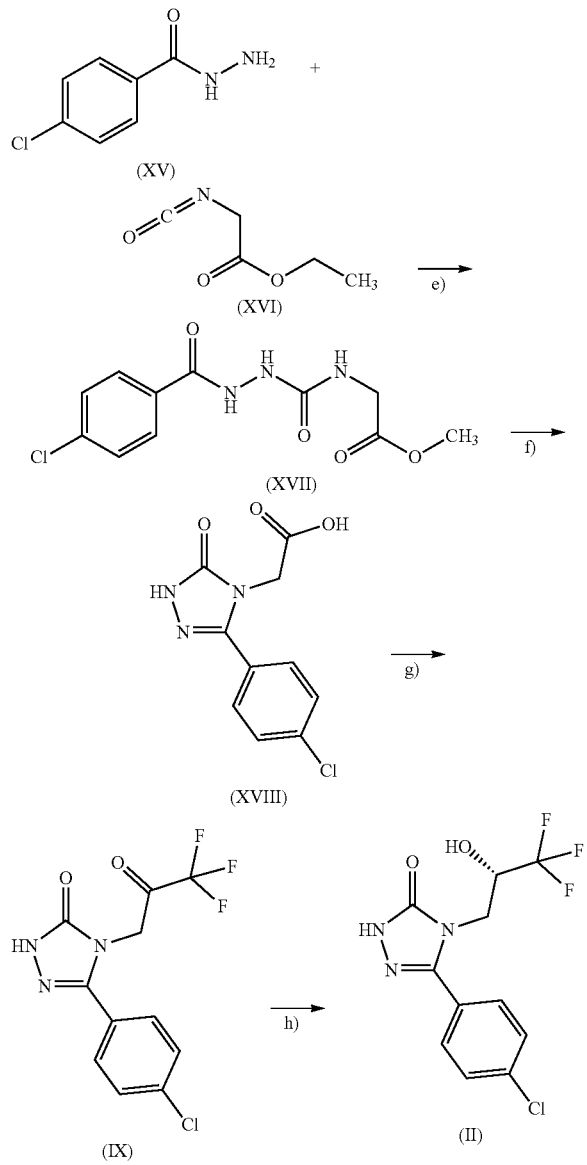

[e) THF; f) aq. NaOH, Δ; g) 1. (CF$_3$CO)$_2$O/pyridine, 2. aq. HCl, Δ; h) chiral Ru(II) catalyst, HCOOH/Et$_3$N.]

The starting substances of the formula (II) are described in WO 2010/105770 (see Schemes 4 and 5; Examples 1A, 2A, 3A, 4A and 158A therein) and WO 2011/104322 (see Scheme 1; Examples 1A, 2A, 3A, 4A and 5A therein). The compounds of the formula (II) are obtained by reacting 4-chlorobenzohydrazide (XV) with ethyl 2-isocyanatoacetate (XVI) to give ethyl N-({2-[(4-chlorophenyl)carbonyl]hydrazinyl}carbonyl)glycinate (XVI). The latter is then converted by a base-induced cyclization reaction to [3-(4-chlorophenyl)-5-oxo-1,5-dihydro-4H-1,2,4-triazol-4-yl] acetic acid (XVIII). 5-(4-Chlorophenyl)-4-(3,3,3-trifluoro-2-oxopropyl)-2,4-dihydro-3H-1,2,4-triazol-3-one (IX) is then obtained by reaction with trifluoroacetic anhydride and subsequent treatment with hydrochloric acid. The ketone (IX) is then converted by an asymmetric transfer hydrogenation by means of an enantioselective ruthenium(II) catalyst to the chiral alcohol (II).

With the novel inventive synthesis, it has been possible to prepare the target compound (I) in a very efficient manner. The process offers considerable advantages over the prior art with regard to scalability and industrial implementation. The overall yield is significantly higher compared to published data; moreover, a very high purity of the active ingredient is generally achieved. One embodiment of the novel process enables the reproducible, economic preparation of the defined crystal form that has not been described before in the prior art. By the inventive process presented here, several kg of material for clinical trials have already been successfully produced.

Preferred salts in the context of the present invention are physiologically acceptable salts of the compounds according to the invention (for example, cf. S. M. Berge et al., "Pharmaceutical Salts", *J. Pharm. Sci.* 1977, 66, 1-19). However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of customary bases, preferred examples being alkali metal salts (e.g. sodium salts and potassium salts), alkaline earth metal salts (e.g. calcium salts and magnesium salts) and ammonium salts, derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the compounds according to the invention which form a complex in the solid or liquid state by coordination with solvent molecules. Hydrates are a specific form of the solvates in which the coordination is with water.

The compounds of the formula (I-A), (XII-A), (XIV-A) and (I-B), (XII-B), (XIV-B) are each a subset of the compounds of the formula (I), (XII) and (XIV) and are each the enantiomers or diastereomers with regard to the stereocentre of the alcohol group in the 5 position of the 1,2,4-triazole ring, or of the protected form thereof. The compounds of the formula (I-A), (XII-A) and (XIV-A) are assigned here to an (S) configuration of the stereocentre, and the compounds of the formula (I-B), (XII-B) and (XIV-A) are each assigned to an (R) configuration of the stereocentre.

If the compounds according to the invention can occur in tautomeric forms, the present invention encompasses all the tautomeric forms.

The following three tautomer representations (a), (b) and (c) of a triazole derivative are equivalent to one another and synonymous and in all cases are descriptive of a 1,4-disubstituted triazole derivative.

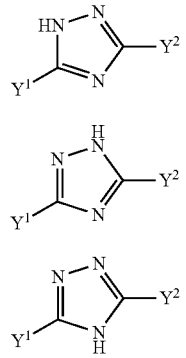

This applies especially to the following structural elements: 1H-1,2,4-triazol-3-yl, 1H-1,2,4-triazol-5-yl, 4H-1,2,4-triazol-3-yl and 4H-1,2,4-triazol-5-yl. $Y^1$ and $Y^2$ here are different substituents.

The present invention provides a process for preparing the compounds of the general formula (I), or the salts thereof, the solvates thereof or the solvates of the salts thereof, characterized in that it comprises steps [C] and [D], wherein

[C] a compound of the general formula (XI)

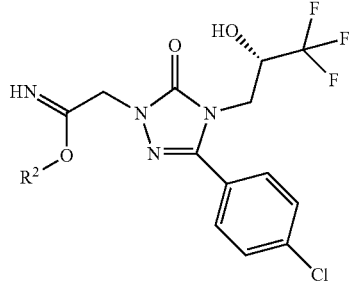

where
$R^2$ is $(C_1-C_4)$-alkyl, preferably methyl.
in a successive manner, is reacted in a first step
[C-1] in the presence of a base with an acid chloride of the general formula (XII)

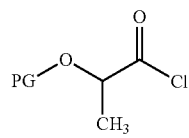

where
PG is a protecting group, preferably acetyl,
and the resultant intermediate is then reacted in a subsequent step

[C-2] in the presence of a base with a phenylhydrazine compound of the general formula (XIII)

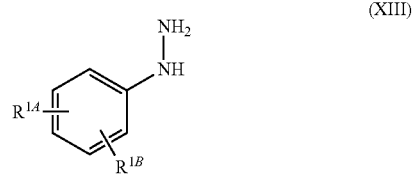

where $R^{1A}$ and $R^{1B}$ are independently selected from the group consisting of hydrogen, fluorine, chlorine, methyl, monofluoromethyl, difluoromethyl, trifluoromethyl, ethyl, methoxy, difluoromethoxy and trifluoromethoxy to give a 1,2,4-triazolyl compound of the general formula (XIV)

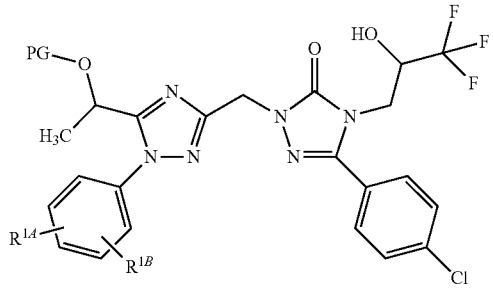

where PG, $R^{1A}$ and $R^{1B}$ have the definitions given above and the latter is converted in a subsequent step

[D] by detachment of the protecting group PG to a compound of the general formula (I)

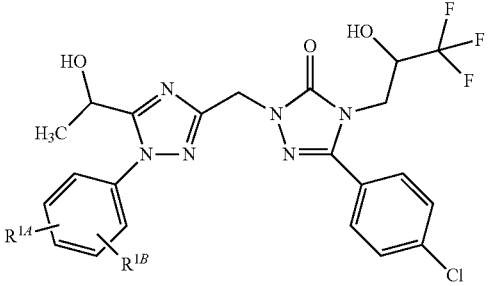

where $R^{1A}$ and $R^{1B}$ have the definitions given above.

By contrast with the prior art (WO 2016/071212), the preparation of (I) (via (XI)+(XII)+(XIII)→(XIV)→(I), see Scheme 3: steps 3+4: 36.7% to 82.2% over 2 stages) proceeds with a much higher yield than for an analogous sequence in the prior art (see Scheme 2: (V)→(VII)→(I), 2.9% to 28.9% over 2 stages).

In an advantageous embodiment, the process according to the invention is conducted as a one-pot reaction in a multistage mode of operation adapted to the chemical mechanism.

In this context, the process is conducted in the presence of a suitable solvent and the intermediate that results from step [C-1] is then converted without isolation, i.e. in solution, in the subsequent step [C-2].

In a further advantageous embodiment, the 1,2,4-triazolyl compound of the general formula (XIV) obtained from step [C-2] is converted without isolation, i.e. in solution, to a compound of the general formula (I) in the subsequent step [D].

In one embodiment, the process according to the invention, prior to step [C], comprises a further step [B] wherein

[B] a compound of the formula (X)

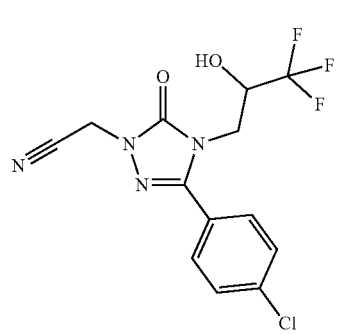

(X)

is reacted with a basic ($C_1$-$C_4$)-alkoxylate, preferably sodium methoxide, to give an imino ester compound of the general formula (XI)

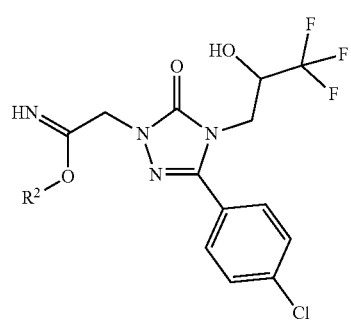

(XI)

where $R^2$ is ($C_1$-$C_4$)-alkyl, preferably methyl.

In an advantageous embodiment, the process according to the invention is conducted as a one-pot reaction in a multistage mode of operation adapted to the chemical mechanism.

In this context, the reaction is conducted in the presence of a suitable solvent and the imino ester compound of the general formula (XI) that results from step [B] is then converted without isolation, i.e. in solution, in a subsequent step [C].

In one embodiment, the process according to the invention comprises, prior to step [C], a step [B] and, prior to step [B], a further step [A], wherein

[A] a compound of the general formula (II)

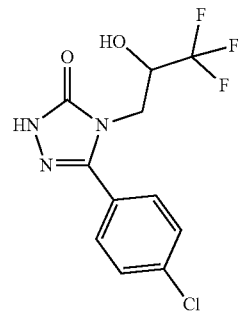

(II)

is reacted with a nitrile compound (IX)

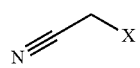

(IX)

where X is a leaving group, preferably chloride or bromide, to give a compound of the general formula (X)

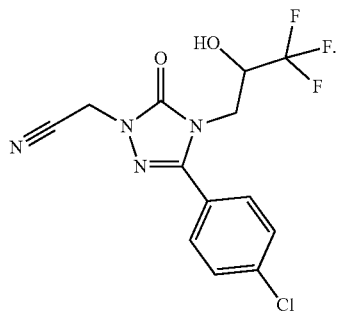

(X)

In a further embodiment of the process according to the invention, this process comprises steps [A], [B], [C] and [D], wherein

[A] a compound of the general formula (II)

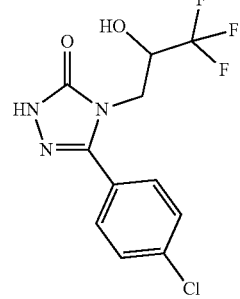

(II)

is reacted with a nitrile compound (IX)

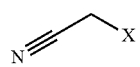

(IX)

where X is a leaving group, preferably chloride or bromide, to give a compound of the general formula (X)

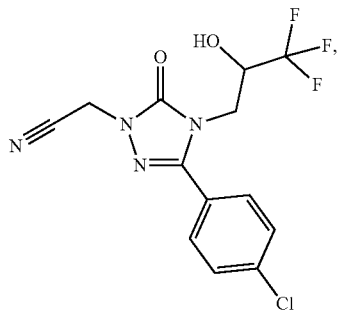
(X)

and the latter is reacted in a subsequent step

[B] with a basic $(C_1-C_4)$-alkoxylate, preferably sodium methoxide, to give an imino ester compound of the general formula (XI)

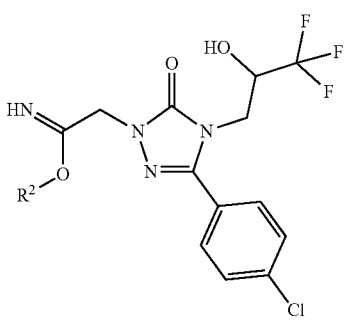
(XI)

where
$R^2$ is $(C_1-C_4)$-alkyl, preferably methyl.
and the latter is reacted in a subsequent step
[C] in a successive manner, in a first step
[C-1] in the presence of a base with an acid chloride of the general formula (XII)

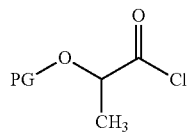
(XII)

where
PG is a protecting group, preferably acetyl,
and the resultant intermediate is then reacted in a subsequent step
[C-2] in the presence of a base with a phenylhydrazine compound of the general formula (XIII)

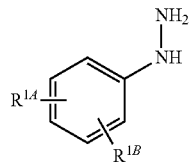
(XIII)

where $R^{1A}$ and $R^{1B}$ are independently selected from the group consisting of hydrogen, fluorine, chlorine, methyl, monofluoromethyl, difluoromethyl, trifluoromethyl, ethyl, methoxy, difluoromethoxy and trifluoromethoxy to give a 1,2,4-triazolyl compound of the general formula (XIV)

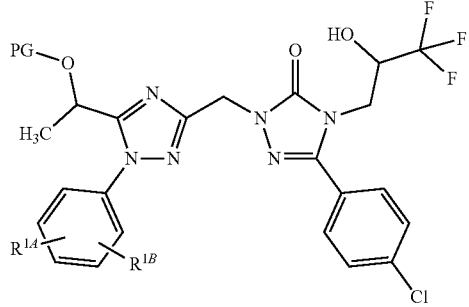
(XIV)

where $R^{1A}$ and $R^{1B}$ have the definitions given above, and
PG is a protecting group, preferably acetyl,
and the latter is reacted in a subsequent step
[D] by detachment of the protecting group PG to give a compound of the general formula (I)

(I)

where $R^{1A}$ and $R^{1B}$ have the definitions given above.

Preference is given to a process for preparing compounds of the formula (I), characterized in that $R^{1A}$ and $R^{1B}$ are independently selected from the group consisting of hydrogen, fluorine and chlorine, where at least one of the substituents is not hydrogen.

Particular preference is given to a process for preparing compounds of the formula (I), characterized in that $R^{1A}$ is hydrogen and $R^{1B}$ is chlorine in the 2 position or in the 3 position.

Very particular preference is given to a process for preparing compounds of the formula (I), characterized in that $R^{1A}$ is hydrogen and $R^{1B}$ is chlorine in the 3 position.

Very particular preference is given to a process for preparing compounds of the formula (I-A-1)

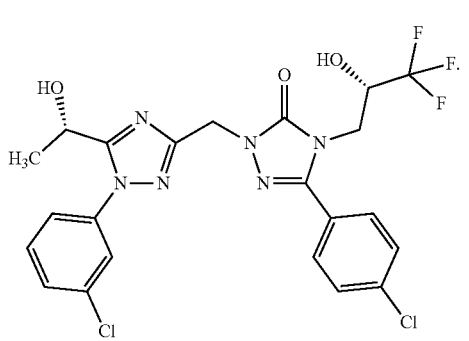
(I-A-1)

The present invention further provides a process for preparing the compounds of the general formula (X), or the salts thereof, the solvates thereof or the solvates of the salts thereof, characterized in that it comprises a step [A], wherein

[A] a compound of the general formula (II)

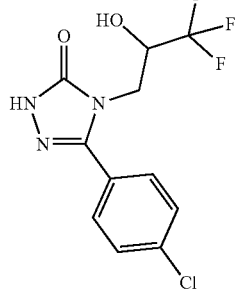

is reacted with a nitrile compound (IX)

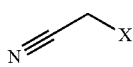

where X is a leaving group, preferably chloride or bromide,
to give a compound of the general formula (X)

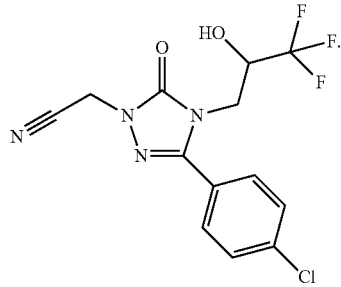

The present invention further provides a process for preparing the compounds of the general formula (XI), or the salts thereof, the solvates thereof or the solvates of the salts thereof, characterized in that it comprises a step [B], wherein

[B] a compound of the formula (X)

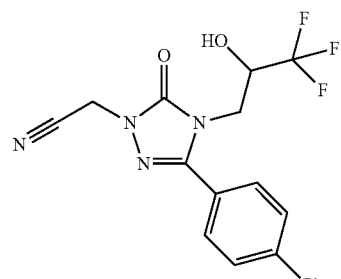

is reacted with a basic $(C_1-C_4)$-alkoxylate, preferably sodium methoxide, to give an imino ester compound of the general formula (XI)

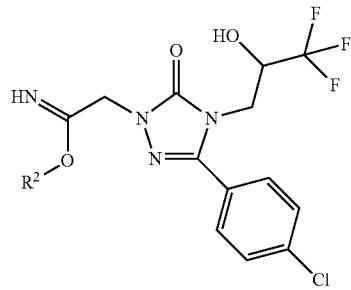

where
$R^2$ is $(C_1-C_4)$-alkyl, preferably methyl.

The present invention further provides a compound of the general formula (X)

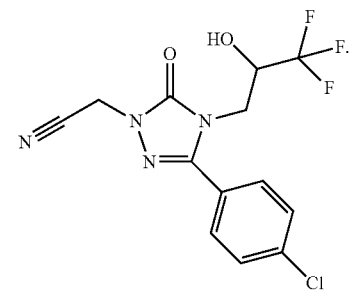

In a preferred embodiment of the present invention, the compound is {3-(4-chlorophenyl)-5-oxo-4-[(2S)-3,3,3-trifluoro-2-hydroxypropyl]-4,5-dihydro-1H-1,2,4-triazol-1-yl}acetonitrile (X-a)

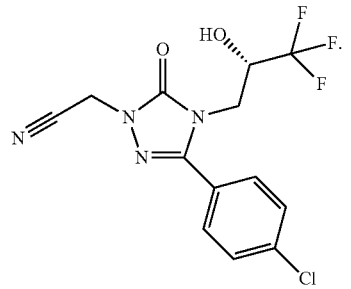

The present invention further provides for the use of a compound of the general formula (X) for preparation of a compound of the general formula (I).

The present invention further provides a compound of the general formula (XI)

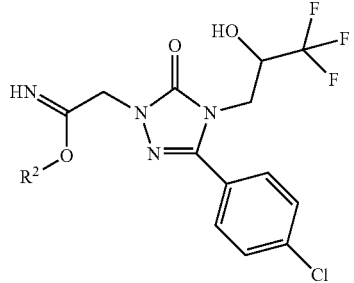

(XI)

where
$R^2$ is $(C_1-C_4)$-alkyl, preferably methyl.

In a preferred embodiment of the present invention, the compound is methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI-a)

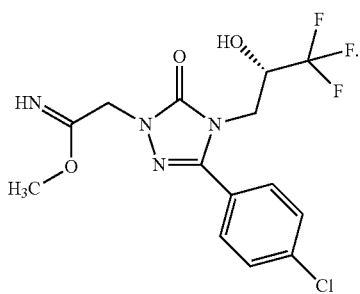

(XI-a)

The present invention further provides for the use of a compound of the general formula (XI) for preparation of a compound of the general formula (I).

The present invention further provides for the use of a compound of the general formula (XIV) for preparation of a compound of the general formula (I).

Step 1:

Suitable bases for process step [A]: (II)+(IX)→(X) are the standard inorganic or organic bases, for example and with preference alkali metal carbonates such as sodium carbonate, potassium carbonate or caesium carbonate, alkali metal alkoxides such as sodium tert-butoxide or potassium tert-butoxide, or organic amines such as N,N-diisopropylethylamine (DIPEA) and triethylamine. Solvents used may be inert solvents, for example acetonitrile, methyl isobutyl ketone, dioxane, dimethylformamide, dimethylacetamide, N-methylpyrrolidinone, dimethyl sulphoxide or sulpholane. Preference is given to using potassium carbonate in methyl isobutyl ketone or acetonitrile.

If appropriate, these process steps can advantageously be conducted with addition of alkylation catalysts, for example lithium bromide, sodium iodide, tetra-n-butylammonium bromide or benzyltriethylammonium chloride. In addition, it may be found to be advantageous to meter in the chloroacetonitrile or bromoacetonitrile alkylating agent over a prolonged period. The reactions are effected generally within a temperature range from +40° C. to +120° C., preferably at +60° C. to +80° C.

The reaction can be performed at standard, elevated or reduced pressure (e.g. from 0.5 to 5 bar); in general, standard pressure is employed.

The compounds of the formula (X) may alternatively also be prepared from compounds of the formula (XX) that are known from the literature (see Scheme 5):

Scheme 5:

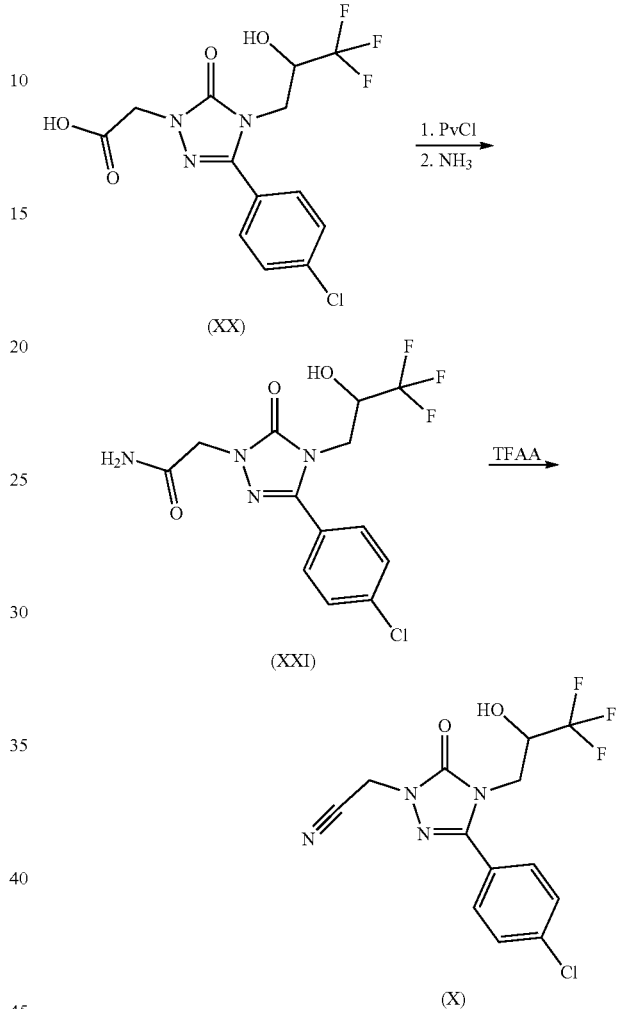

[PvCl = pivaloyl chloride, TFAA = trifluoroacetic anhydride].

The coupling reaction (XX)→(XXI) [amide formation] can be effected either by a direct route with the aid of a condensing or activating agent in the presence of a base or via the intermediate stage of a carbonyl chloride, carboxylic ester or carbonyl imidazolide obtainable from (XX).

Suitable condensing or activating agents of this kind are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), isopropyl chloroformate or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, α-chloroenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (T3P, PPACA), diethyl cyanophosphonate, diphenylphosphoryl azide (DPPA), bis(2-oxo-3-oxazolidinyl)phosphoryl chloride, benzotriazol-1-yloxytris (dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N'N'-tetramethyluronium tetrafluoroborate (TBTU), O-(benzotriazol-1-yl)-N,N,N'N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and suitable bases are alkali metal carbonates, e.g. sodium or potassium carbonate, or tertiary amine bases such as triethylamine, N-methylmorpholine (NMM), N-methylpiperidine (NMP), N,N-diisopropylethylamine (DIPEA), pyridine or 4-N,N-dimethylaminopyridine (DMAP). Typically, the acid chlorides are prepared by reaction with thionyl chloride or oxalyl chloride in an inert solvent such as dichloromethane or N,N-dimethylformamide. It is likewise possible to use mixtures of the solvents listed.

The conversion to the nitrile (XXI)→(X) can be conducted in the presence of a dehydrating agent. Typical dehydrating agents are, for example, trifluoroacetic anhydride (TFAA), phosphorus pentoxide ($P_4O_{10}$), phosphoryl chloride ($POCl_3$), phosphorus pentachloride ($PCl_5$), $CCl_4$—$PPh_3$ (Appel's reagent), hexamethylphosphoramide (HMPA); methyl N-(triethylammonium sulphonyl)carbamate (Burgess reagent), (chloromethylene)dimethyliminium chloride (Vilsmeier reagent), oxalyl chloride/DMSO and thionyl chloride ($SOCl_2$).

Typical solvents for the two process steps (XX)→(XXI) and (XXI)→(X) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, dimethyl sulphoxide, N,N-dimethylformamide, N,N'-dimethylpropyleneurea (DMPU), N-methylpyrrolidone (NMP) or pyridine. It is equally possible to use mixtures of the solvents mentioned.

Typically and with preference, the carboxylic acid (XX) is reacted in a first step with pivaloyl chloride in the presence of pyridine, giving an intermediate which is reacted with ammonia in a subsequent step. Typically, the intermediate formed is not isolated and the reaction is conducted as a one-pot reaction over the two stages. Suitable bases for the first step are preferably pyridine, 4-(N,N-dimethylamino) pyridine or N,N-diisopropylethylamine (DIPEA). The conversion of carboxamide (XX) to the nitrile (X) is then typically effected via the reaction with trifluoroacetic anhydride. Both reactions are conducted in an inert organic solvent, preferably tetrahydrofuran.

Compounds of the formula (XX) are known from the literature (see WO 2010/105770, Scheme 2, Examples 8A and 9A; and WO 2011/104322, Scheme 11).

Step 2:

Bases which can be used for the preparation of the imino ester (XI) in process step [B] are basic ($C_1$-$C_4$)-alkali metal alkoxides, for example sodium methoxide, sodium ethoxide, sodium propoxide, sodium isopropoxide, sodium tert-butoxide or potassium tert-butoxide. Suitable alcohols are alcohols such as methanol, ethanol, n-propanal, 2-propanal, n-butanol, 2-butanol and tert-butanol. Preference is given to using sodium methoxide in methanol.

The reactions are generally effected within a temperature range from +20 to +80° C., preferably from +40 to +60° C. The imino ester (XI) need not be intermediately isolated, but can be used directly in the subsequent stage by distilling methanol off and changing the solvent to toluene or tetrahydrofuran.

Step 3:

The multicomponent cyclization reaction in process step [C] is effected in a two-stage process. First of all, in process step [C-1], the imino ester (XI) is reacted with the acid chloride (XII) in the presence of a base and the resultant intermediate is then reacted with the phenylhydrazine compound (XIII) in the presence of a base in process step [C-2]. Typically, the intermediate formed is not isolated and the two-stage process is conducted as a one-pot reaction.

Advantageously, the acid chloride (XII) is used here in step [C-1] in an amount of 1.1 to 1.5 mol, preferably in an amount of 1.2 mol, based on 1 mol of the compound of the formula (XI). The base is typically used in step [C-1] in an amount of 1 to 2.5 mol, preferably in an amount of 1.05 to 2.0 mol, more preferably in an amount of 1.05 to 1.5 mol, based on 1 mol of the compound of the formula (XII).

The hydrazine (XIII) in step [C-2] can also be used in salt form, for example as the hydrochloride or as the p-toluenesulphonic salt (tosylate). Under the basic reaction conditions, the salt form is then converted to the free hydrazine. The amount of base can be adjusted correspondingly in this case. In a further advantageous embodiment, the hydrazine salt is neutralized prior to addition in a separate reaction vessel and the resulting solution is then added to the reaction mixture as a solution, optionally after removal of the salt formed by filtration.

The base is typically used in step [C-2] in an amount of 1.05 to 1.5 mol, preferably in an amount of 1.2 to 1.5 mol, based on 1 mol of the compound of the formula (XIII).

Suitable bases for the two steps are typically tertiary amine bases, for example N,N-diisopropylethylamine (DIPEA), triethylamine, triisopropylamine, N-methylimidazole, N-methylmorpholine, pyridine and 4-(dimethylamino) pyridine. Preference is given to triethylamine or N,N-diisopropylethylamine. Particular preference is given to diisopropylethylamine.

Suitable solvents are inert organic solvents, for example dichloromethane, 1,2-dichloroethane, methyl tert-butyl ether, tetrahydrofuran, 1,4-dioxane, 1,2-dimethoxymethane, toluene, pyridine, ethyl acetate, acetonitrile or N,N-dimethylformamide or mixtures of these solvents.

Preference is given to using tetrahydrofuran (THF) or mixtures of tetrahydrofuran and toluene.

The reaction with the acid chloride (XII) in step [C-1] and with the hydrazine (XIII) in step [C-2] is effected within a temperature range from −20° C. to +30° C., preferably from 0° C. to +10° C. For triazole formation with elimination of water (cyclization) in step [C-2], the reaction mixture is subsequently brought to a temperature of +20 to +150° C. Preferably, the reaction is conducted at a temperature of +70 to +80° C.

Step 4:

The introduction and detachment of the protecting group PG in process step [D] is effected by standard literature methods [see, for example, T. W. Greene and P. G. M. Wuts, *Protective Groups in Organic Synthesis*, Wiley, New York, 1999]. For instance, the acetyl group is preferably removed with a base, for example aqueous sodium hydroxide solution.

When the protecting group detachment in process step [D] is conducted with aqueous sodium hydroxide solution, the workup is effected, for example, by extraction with a suitable solvent, followed by repeated washing and drying. Preference is given to extraction with methyl tert-butyl ether (MtBE).

The compounds of the formulae (II), (IX), (XII), (XIII) and (XX) are either commercially available or described as such in the literature, or they can be prepared in a way obvious to the person skilled in the art, in analogy to methods published in the literature. Numerous detailed methods and literature information for preparation of the starting materials can also be found in the Experimental.

Since the compound of the formula (I-A-1) is being developed in the form of a tablet, there is a high demand for reproducible isolation of the isolated compound of the formula (I-A-1) in a defined crystalline form, such that reproducible bioavailability can be assured.

It has been found that, surprisingly, the compound (5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one of the formula (I-A-1)

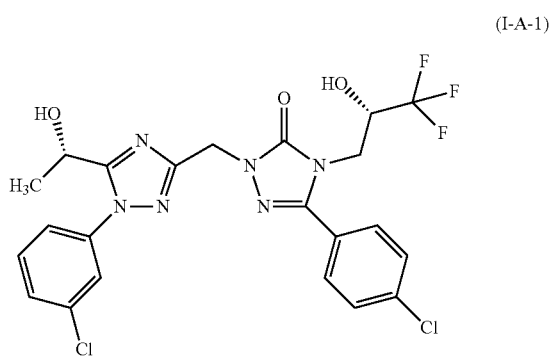 [SMILES: C[C@H](O)c1nc(Cn2nc(-c3ccc(Cl)cc3)n(C[C@H](O)C(F)(F)F)c2=O)nn1-c1cccc(Cl)c1]

(I-A-1)

can crystallize out of a mixture of methyl tert-butyl ether/diisopropyl ether or out of a mixture of methyl tert-butyl ether/n-heptane, with reproducible formation of crystalline polymorph I (Step 5).

Step 5:

A solution of the compound of the formula (I-A-1) in a 5- to 10-fold excess of methyl tert-butyl ether (MtBE) is stirred here at 20 to 80° C., preferably at 50 to 60° C. and more preferably at reflux temperature of the methyl tert-butyl ether (about 54° C.), and admixed with diisopropyl ether at this temperature. With continued addition of diisopropyl ether, MtBE is distilled off. In the course of this, the compound of the formula (I-A-1) crystallizes out. The system is cooled to a temperature of 0 to 30° C., preferably 10 to 20° C., and the crystals are isolated and dried under reduced pressure at 40 to 60° C., preferably at 40 to 50° C.

Alternatively, it is also possible to use a mixture of methyl tert-butyl ether/n-heptane. Here, a solution of the compound of the formula (I-A-1) in a 5- to 10-fold excess of methyl tert-butyl ether (MtBE) is stirred at 20 to 80° C., preferably at 50 to 60° C. and more preferably at reflux temperature of the methyl tert-butyl ether (about 54° C.), and admixed with 1.5 to 2.5 times the volume of n-heptane at this temperature, and the compound of the formula (I-A-1) crystallizes out.

The system is cooled to a temperature of 0 to 30° C., preferably 10 to 20° C., and the crystals are isolated and dried under reduced pressure at 40 to 80° C., preferably at 40 to 50° C.

For GMP-related reasons, it may be advisable to subject the product solution in MtBE first to a particle filtration prior to the heating.

The workup is generally effected by filtration, repeated washing with diisopropyl ether or n-heptane, and subsequent drying.

The achieved chemical purity of >99% and the content of about 100% meet the criteria for commercial products according to ICH guidelines. The optical purity is >>99% e.e.

The crystallization process is very robust and delivers the desired crystal form in a reproducible manner. The compound of the formula (I) is generally micronized and formulated pharmaceutically to tablets. It has been found that the crystal form has very good stability properties (even at high humidity) and can be stored without loss of stability over several months.

The present invention further provides the compound (5-(4-chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one of the formula (I-A-1) in crystalline form of polymorph I.

The present invention provides the compound of the formula (I-A-1) in crystalline form of polymorph I, characterized in that the x-ray diffractogram of the compound has peak maxima of the 2 theta angle at 7.0, 8.9, 16.8, 17.7, 17.9, 18.1, 21.6, 21.8, 22.4 and 24.6.

The present invention further provides a process for preparing the compound of the formula (I-A-1) in crystalline form of polymorph I, characterized in that the compound of the formula (I-A-1), present in one or more polymorphs or in solvate form, is stirred in a mixture of methyl tert-butyl ether/diisopropyl ether or of methyl tert-butyl ether/n-heptane at a temperature of 20° C. to 80° C., then filtered, washed and dried under reduced pressure.

A preferred solvent for the process for preparing the compounds of the formula (I-A-1) in crystalline form of polymorph I is a mixture of methyl tert-butyl ether/diisopropyl ether or a mixture of methyl tert-butyl ether/n-heptane.

A preferred temperature range for the process for preparing the compound of the formula (I-A -1) in crystalline form of polymorph I is at the reflux temperature of methyl tert-butyl ether (at about 54° C.).

The present invention further provides the compound of the formula (I-A-1) in crystalline form of polymorph I as described above for treatment of disorders.

The present invention further provides a medicament comprising a compound of the formula (I-A-1) in crystalline form of polymorph I as described above and no major proportions of any other form of the compound of the formula (I-A-1) than the crystalline form of polymorph I as described above. The present invention further provides a medicament comprising a compound of the formula (I-A-1) in crystalline form of polymorph I as described above in more than 90 percent by weight based on the total amount of the compound of the formula (I-A-1) present.

The present invention further provides for the use of the compound of the formula (I-A-1) in crystalline form of polymorph I as described above for production of a medicament for treatment of cardiovascular disorders and renal disorders.

The present invention further provides the method for treatment of cardiovascular disorders and renal disorders by administering an effective amount of a compound of the formula (I-A -1) in crystalline form of polymorph I as described above.

The inventive compounds of the formula (I-A-1) act as potent dual V1a/V2 receptor antagonists and exhibit an unforeseeable, valuable spectrum of pharmacological action. They are therefore suitable for use as medicaments for treatment and/or prophylaxis of diseases in humans and animals.

The compounds according to the invention, on their own or in combination with one or more other active ingredients, are suitable for prevention and/or treatment of various disorders, for example disorders of the cardiovascular system (cardiovascular disorders), for cardioprotection after damage to the heart and of metabolic and kidney disorders.

The compounds according to the invention, on their own or in combination with one or more other active ingredients, are suitable for prevention and/or treatment of various disorders, for example disorders of the cardiovascular system (cardiovascular disorders), and of renal disorders.

The compounds according to the invention have valuable pharmacological properties and can be used for prevention and/or treatment of various disorders and disease-related conditions in humans and animals.

Possible target indications are listed by way of example and with preference in WO 2016/071212, pages 16 to 19.

Suitable combination active ingredients and dosage forms are listed by way of example and with preference in WO 2016/071212, pages 19 to 27.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

A. EXAMPLES

Abbreviations aq. aqueous, aqueous solution
c concentration
cat. catalytic
CDI N,N'-carbonyldiimidazole
DCI direct chemical ionization (in MS)
dist. distilled
DIEA N,N-diisopropylethylamine
DMAP 4-N,N-dimethylaminopyridine
DMF dimethylformamide
DMSO dimethyl sulphoxide
ee enantiomeric excess
ent enantiomerically pure, enantiomer
eq. equivalent(s)
ESI electrospray ionization (in MS)
Et ethyl
GC-MS gas chromatography-coupled mass spectrometry
h hour(s)
HPLC high-pressure, high-performance liquid chromatography
conc. concentrated
LC-MS liquid chromatography-coupled mass spectrometry
Me methyl
min minute(s)
MS mass spectrometry
MtBE methyl tert-butyl ether
NMR nuclear magnetic resonance spectrometry
Ph phenyl
quant. quantitative (in yield)
rac racemic, racemate
RT room temperature
$R_t$ retention time (in HPLC)
THF tetrahydrofuran
UV ultraviolet spectrometry
v/v volume to volume ratio (of a solution)

LC/MS and HPLC Methods:

Method 1 (LC/MS): MCW-SQ-HSST3

Instrument: Waters Acquity SQD UPLC System; column: Waters Acquity UPLC HSS T3 1.8 μ, 50 mm×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2 (LC/MS): MCW-FT-MS-M1

Instrument: Thermo Scientific FT-MS; instrument UHPLC+: Thermo Scientific UltiMate 3000; column: Waters, HSST3, 2.1×75 mm, C18 1.8 μm; Eluent A: 1 l water+0.01% formic acid; eluent B: 1 l acetonitrile+0.01% formic acid; gradient: 0.0 min 10% B→2.5 min 95% B→3.5 min 95% B; oven: 50° C.; flow: 0.90 ml/min; UV detection: 210 nm/Optimum Integration Path 210-300 nm Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

In the case of purifications of compounds of the invention by preparative HPLC by the above-described methods in which the eluents contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the centre of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

The $^1$H NMR data of selected examples are stated in the form of $^1$H NMR peak lists. For each signal peak, first the δ value in ppm and then the signal intensity in round brackets are listed. The δ value/signal intensity number pairs for different signal peaks are listed with separation from one another by commas. The peak list for an example therefore takes the following form: $δ_1$ (intensity$_1$), $δ_2$ (intensity$_2$), . . . . , $δ_i$ (intensity$_i$), . . . . , $δ_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the 1H NMR peaks are similar to the conventional 1H NMR printouts and thus usually contain all peaks listed in a conventional NMR interpretation. In addition, like conventional 1H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional 1H NMR interpretation. A detailed description of the presentation of NMR data in the form of peak lists can be found in the publication "Citation of NMR Peaklist Data within Patent Applications" (cf. Research Disclosure Database Number 605005, 2014, 1 Aug. 2014 or _http:// world wide web. researchdisclosure. com/ searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "MinimumHeight" to values of <1%.

Melting points and melting point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

WORKING EXAMPLES

Example 1

{3-(4-Chlorophenyl)-5-oxo-4-[(2S)-3,3,3-trifluoro-2-hydroxypropyl]-4,5-dihydro-1H-1,2,4-triazol-1-yl}acetonitrile (X-a)

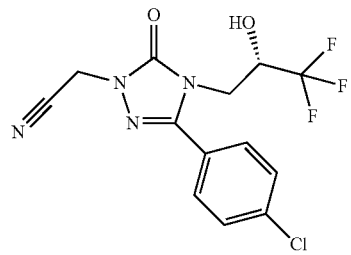 [SMILES: N#CCn1nc(-c2ccc(Cl)cc2)n(C[C@H](O)C(F)(F)F)c1=O]

100 g (0.325 mol) of 5-(4-chlorophenyl)-4-((2S)-3,3,3-trifluoro-2-hydroxypropyl)-2,4-dihydro-3H-1,2,4-triazol-3-one (II-A) (synthesis described as Example 5A in WO 2010/105770 A1) as a solution in 1.0 l of methyl isobutyl ketone were initially charged together with 135 g (0.975 mol) of sodium carbonate and then the mixture was heated to 60° C. Subsequently, at this temperature, 27 g (0.358 mol) of chloroacetonitrile dissolved in 270 ml of methyl isobutyl ketone (IX) were homogeneously added dropwise over a period of 6 h. The mixture was stirred at 60° C. for a further 15 h and then cooled to 20° C., 500 ml of water were added, the mixture was stirred and the organic phase was removed. The organic phase was washed once again with 500 ml of water, and then concentrated to a volume of about 250 ml under reduced pressure at a jacket temperature of 60° C. Subsequently, 250 ml of n-heptane were added, and the product crystallized out. To complete the crystallization, with simultaneous addition of 500 ml of n-heptane at a jacket temperature of 60° C., about 500 ml of the solvent mixture were distilled off under reduced pressure. The mixture was cooled to 20° C. and stirred at this temperature for one hour. The product was filtered off and washed with n-heptane (2×150 ml). The product was dried at 40° C. under reduced pressure. Yield: 81 g (72% of theory) of a solid.

MS (EIpos): m/z=347.1 [M+H]+

1H-NMR (400 MHz, DMSO-d6): δ=3.81 (dd, 1H), 3.98 (dd, 1H), 4.23-4.34 (m, 1H), 5.17 (s, 2H), 6.91 (d, 1H), 7.55 (d, 2H), 7.78 (d, 2H).

Example 2

Methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI-a)

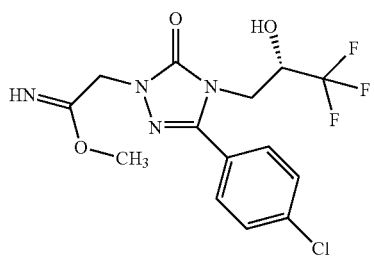 [SMILES: COC(=N)Cn1nc(-c2ccc(Cl)cc2)n(C[C@H](O)C(F)(F)F)c1=O]

200 g (576.9 mmol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (X-a) were initially charged as a solution in 1.6 l of methanol, and 5.2 g (28 mmol) of sodium methoxide (30% in methanol) were added. The mixture was stirred at 50° C. for 2 hours and then concentrated at a jacket temperature of 50° C. to give the oily residue. 2 l of MtBE were added and the mixture was concentrated to a volume of about 0.8 l. The solution was then gradually metered into 4 l of n-hexane while stirring. In the course of this, the product crystallized out as a thick crystal suspension. The mixture was left to cool to 20° C. and stirred at room temperature for one hour. The product was filtered off and washed with n-hexane (2×0.25 l). The product was dried at 40° C. under reduced pressure. Yield: 175 g (80% of theory) of a solid.

1H-NMR (400 MHz, DMSO-d6): δ=3.67 (s, 3H), 3.81 (dd, 1H), 3.96 (dd, 1H), 4.23-4.35 (m, 1H), 4.50 (s, 2H), 6.93 (br. s, 1H), 7.62 (d, 2H), 7.78 (d, 2H), 8.01 (s, 1H).

Example 3

(5-(4-Chlorophenyl)-2-({1-(3-chlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-1)

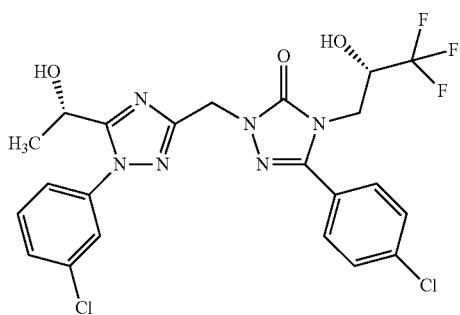 [SMILES: C[C@H](O)c1nc(Cn2nc(-c3ccc(Cl)cc3)n(C[C@H](O)C(F)(F)F)c2=O)nn1-c1cccc(Cl)c1]

Process Variant B:

Methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI-a) (164 g, 433 mmol) was dissolved in a mixture of THF (1.0 l) and toluene (0.5 l). The mixture was admixed with N-ethyldiisopropylamine (97.8 g, 757 mmol) and then stirred at 20° C. for 15 min. Subsequently, at 0° C., (S)-2-acetoxypropionyl chloride (XII-A) (78.2 g, 519 mmol) was metered in and the mixture was stirred at 0° C. for 1 h. Subsequently, at 0° C., a solution of 4-chlorophenylhydrazine hydrochloride (XIII-1) (85.2 g, 476 mmol) and N-ethyldiisopropylamine (67.11 g, 519 mmol) in THF (0.5 l) was metered in, with removal of precipitated N-ethyldiisopropylamine hydrochloride prior to the metered addition, then the mixture was stirred at 20° C. for 1 h and at reflux temperature (about 75° C.) for a further 2 h. The mixture was left to cool to 20° C. and 0.75 l of water was added to the mixture. After phase separation, the organic phase was washed twice with 0.5 l each time of a 1 N hydrochloric acid solution, and then the mixture was concentrated under reduced pressure to the oily residue at a jacket temperature of 80° C. and co-distilled twice with 1.0 l each time of methanol. The oily residue was then dissolved in 0.6 l of methanol, 0.5 l of a 1 N sodium hydroxide solution was added at 0° C., and the mixture was stirred at 20° C. for 1 h. After addition of 0.75 l of water and 0.75 l of MtBE, the organic phase was removed, washed twice with 0.3 l each time of semi-saturated aqueous sodium chloride solution, and then concentrated at a jacket temperature of 80° C. under reduced pressure down to a volume of about 0.3 l. After addition of 1.5 l of diisopropyl ether, the mixture was again concentrated at a jacket temperature of 80° C. under reduced pressure down to a volume of about 0.3 l, and the product precipitates out. The mixture was cooled to 10° C. and stirred at this temperature for one hour. The product was filtered off and washed with 0.3 l of diisopropyl ether. The product was dried at 50° C. under reduced pressure. Yield: 200 g (72% of theory).

MS (ESIpos): m/z (%)=543.1 (100) [M+H]$^+$.

1H-NMR (400 MHz, DMSO-d6): δ=1.47 (d, 3H), 3.85 (dd, 1H), 4.00 (dd, 1H), 4.24-4.36 (m, 1H), 4.81 (quin, 1H), 5.07 (s, 2H), 5.75 (d, 1H), 6.89 (d, 1H), 7.54-7.66 (m, 5H), 7.72-7.79 (m, 3H).

Process Variant C (with Subsequent Crystallization from Methyl Tert-Butyl Ether/Diisopropyl Ether):

1.373 kg (3.96 mol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (X-a) were initially charged as a solution in 6.9 l of methanol, and 36 g (0.198 mol) of sodium methoxide (30% in methanol) were added. The mixture was stirred at 50° C. for 1.5 hours and then concentrated at a jacket temperature of 50° C. to give the still-stirrable, slurry-like residue. Three times, 3.0 l of toluene were added and the mixture was concentrated to a volume of 5 l in each case. THF (9.5 l) and toluene (2.5 l) were added to the residue, N-ethyldiisopropylamine (0.896 kg, 6.93 mol) was added at 20° C., and the mixture was stirred at 20° C. for a further 15 min. Subsequently, at 0° C., (S)-2-acetoxypropionyl chloride (XII-A) (0.715 kg, 4.752 mol) was metered in and the mixture was stirred at 0° C. for 1 h. Subsequently, at 0° C., a solution of 4-chlorophenylhydrazine hydrochloride (XIII-1) (0.78 kg, 4.356 mol) and N-ethyldiisopropylamine (0.614 kg, 4.752 mol) in THF (4.5 l) was metered in, with removal of precipitated N-ethyldiisopropylamine hydrochloride prior to the metered addition, then the mixture was stirred at 20° C. for 1 h and at reflux temperature (about 75° C.) for a further 2 h. The mixture was left to cool to 20° C. and 7.0 l of water were added to the mixture. After phase separation, the organic phase was washed twice with 3.5 l each time of a 1 N hydrochloric acid solution, and the mixture was concentrated under reduced pressure to the oily residue at a jacket temperature of 80° C. and co-distilled twice with 13.5 l each time of methanol. The oily residue was dissolved in 5.5 l of methanol, 4.0 l of a 1 N sodium hydroxide solution was added at 0° C., and the mixture was stirred at 20° C. for 1 h. After addition of 7.0 l of water and 7.0 l of MtBE, the organic phase was removed, washed twice with 2.75 l each time of semi-saturated aqueous sodium chloride solution, and concentrated at a jacket temperature of 80° C. under reduced pressure down to a volume of about 3.0 l. After addition of 16.0 l of diisopropyl ether, the mixture was again concentrated at a jacket temperature of 80° C. under reduced pressure down to a volume of about 6.0 l, and the product precipitated out. The mixture then was cooled to 10° C. and stirred at this temperature for one hour. The product was filtered off and washed twice with 1.0 l each time of diisopropyl ether. The product was dried at 50° C. under reduced pressure. Yield: 1.680 kg (78% of theory).

Purity of >99%; optical purity >>99% e.e.

Process Variant C (with Subsequent Crystallization from Methyl Tert-Butyl Ether/n-Heptane):

50 g (144 mmol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (X-a) were initially charged as a solution in 250 ml of methanol, and 1.58 g (7.3 mmol) of sodium methoxide (25% in methanol) were added. The mixture was stirred at 50° C. for 1.5 hours and then concentrated at a jacket temperature of 50° C. to give the still-stirrable, slurry-like residue. Three times, the mixture was admixed with 200 ml each time of DMF and concentrated to dryness under reduced pressure. 325 ml of THF were added to the residue, N-ethyldiisopropylamine (44 ml, 253 mmol) was added at 20° C., and the mixture was stirred at 20° C. for a further 15 min. Subsequently, at 0° C., (S)-2-acetoxypropionyl chloride (XII-A) (26 g, 173 mmol) was metered in and the mixture was stirred at 0° C. for 1 h. Subsequently, at 0° C., a solution of 4-chlorophenylhydrazine hydrochloride (XIII-1) (28.5 g, 159 mmol) and N-ethyldiisopropylamine (30 ml, 172 mmol) in 150 ml of THF was metered in, with removal of precipitated N-ethyldiisopropylamine hydrochloride prior to the metered addition. Subsequently, the mixture was stirred at 20° C. for 30 min and at reflux temperature (about 75° C.) for a further 2.5 h. The mixture was left to cool to 20° C. and 125 ml of MtBE and 250 ml of water were added to the mixture. After phase separation, the organic phase was washed twice with 125 g each time of a 1 N hydrochloric acid solution, and the mixture was concentrated under reduced pressure to the oily residue at a jacket temperature of 60° C. and co-distilled twice with 500 ml each time of methanol. The oily residue was dissolved in 200 ml of methanol, 35 ml of a 1 N sodium hydroxide solution were added at 0° C., and the mixture was stirred at 20° C. for 1 h. After addition of 175 ml of water and 375 ml of MtBE, the organic phase was removed, washed twice with 62 ml each time of semi-saturated aqueous sodium chloride solution, and concentrated at a jacket temperature of 80° C. under reduced pressure to an oily residue. After addition of 300 ml of diisopropyl ether, the mixture was again concentrated at a jacket temperature of 80° C. under reduced pressure down to a volume of about 150 ml, and the product precipitates out. The mixture then was cooled to 10° C. and stirred at this temperature for one hour. The product was filtered off and washed twice with 100 ml each time of diisopropyl ether. The product was dried at 50° C. under reduced pressure. The crystals were dissolved in 420 ml of MtBE under reflux. After addition of 900 ml of n-heptane at 50° C., the product crystallizes out. The mixture then was cooled to 20° C. and stirred at this temperature for one hour. The product was filtered off, washed with 100 ml of n-heptane and dried at 70° C. under reduced pressure. Yield: 58 g (74% of theory).

Purity of >99%; optical purity >>99% e.e.

Example 4 a) (1R)-1-[1-(3-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]ethyl Acetate (XIV-B-1)

While cooling with ice, 87 mg (0.58 mmol) of (R)-(-)-2-acetoxypropionyl chloride (XII-B) were added dropwise to a mixture of 200 mg (0.53 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 262 µl (1.5 mmol) of DIPEA in 2 ml of THF. After 1 h at 0° C., 104 mg (0.58 mmol) of 3-chlorophenylhydrazine (XIII) were added and then the mixture was stirred at RT overnight. The reaction mixture was purified by chromatography (preparative HPLC, eluent: acetonitrile/water gradient, 0.1% formic acid). Lyophilization of the product-containing fractions gave 208 mg (64% of theory) of the title compound.

LC-MS (Method 2): $R_t$=2.04 min; MS(ESIpos): m/z=585.1 [M+H]$^+$ $^1$H NMR (DMSO-$d_6$, 400 MHz): δ=7.90-7.37 (m, 8H), 6.89 (d, 1H), 5.91 (d, 1H), 5.09 (s, 2H), 4.40-4.20 (m, 1H), 4.09-3.71 (m, 2H), 1.81 (s, 3H), 1.56 (d, 3H)

b) 2-({1-(3-Chlorophenyl)-5-[(1R)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (I-B-1)

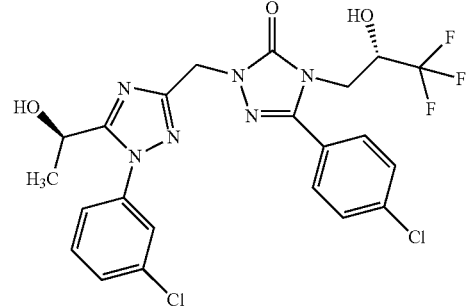 [SMILES: C[C@@H](O)c1nc(Cn2nc(-c3ccc(Cl)cc3)n(C[C@H](O)C(F)(F)F)c2=O)nn1-c1cccc(Cl)c1]

A mixture of 200 mg (0.34 mmol) of the compound from step a) and 341 µl (0.34 mmol) of 1 M sodium hydroxide solution in 2.6 ml of methanol was stirred at RT for 30 min. 1 g of activated ion exchanger (Dowex 50WX8, 200-400 mesh) was added and the mixture was stirred at RT for 5 min. The ion exchanger was then filtered off, and washed with methanol. The filtrate was concentrated. This gave 168 mg (90% of theory) of the title compound.

LC-MS (Method 2): $R_t$=1.85 min; MS(ESIpos): m/z=543.1 [M+H]$^+$ $^1$H NMR (DMSO-$d_6$, 400 MHz): δ=7.98-7.48 (m, 8H), 6.90 (d, 1H), 5.76 (d, 1H), 5.07 (s, 2H), 4.81 (t, 1H), 4.46-3.68 (m, 3H), 1.47 (d, 3H).

Example 5 a) (1S)-1-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(2,4-dichlorophenyl)-1H-1,2,4-triazol-5-yl]ethyl Acetate (XIV-A-2)

While cooling with ice, 73 µl (0.58 mmol) of (S)-(-)-2-acetoxypropionyl chloride (XII-A) were added dropwise to a mixture of 200 mg (0.53 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 262 µl (1.51 mmol) of DIPEA in 2 ml of THF. After 1 h at 0° C., 124 mg (0.58 mmol) of 2,4-dichlorophenylhydrazine hydrochloride (XIII) were added and then the mixture was stirred at RT overnight. The reaction mixture was heated under reflux for 2 h and heated in the microwave at 100° C. for 5 h. The solvent was removed under reduced pressure and the crude product was purified by chromatography (preparative HPLC, eluent: acetonitrile/water gradient, 0.1% formic acid). Lyophilization of the product-containing fractions gave 163 mg (48% of theory) of the title compound.

LC-MS (Method A): $R_t$=1.13 min; MS(ESIpos): m/z=619.0 [M+H]$^+$ $^1$H NMR (DMSO-d$_6$, 400 MHz): δ=8.04-7.49 (m, 7H), 6.89 (d, 1H), 5.90-5.44 (m, 1H), 5.10 (d, 2H), 4.45-4.16 (m, 1H), 4.11-3.73 (m, 2H), 1.81 (s, 3H), 1.53 (d, 3H)

b) 5-(4-Chlorophenyl)-2-({1-(2,4-dichlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-2)

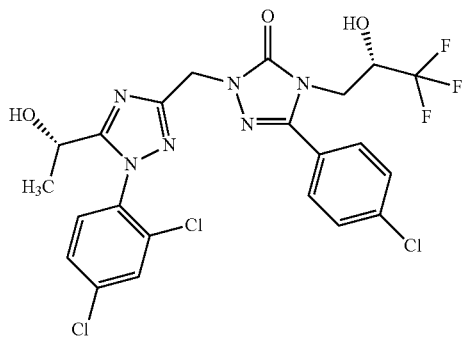 [SMILES: C[C@H](O)c1nc(Cn2nc(-c3ccc(Cl)cc3)n(C[C@H](O)C(F)(F)F)c2=O)nn1-c1ccc(Cl)cc1Cl]

A mixture of 160 mg (0.26 mmol) of the compound from step a) and 258 µl (0.26 mmol) of 1 M sodium hydroxide solution in 2 ml of methanol was stirred at 0° C. for 2 min and at RT for 90 min. 1 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 148 mg (quant.) of the title compound.

LC-MS (Method A): $R_t$=1.02 min; MS(ESIpos): m/z=577.1 [M+H]$^+$ $^1$H NMR (DMSO-d$_6$, 400 MHz): δ=7.92 (d, 1H), 7.78-7.71 (m, 2H), 7.68-7.58 (m, 4H), 6.89 (d, 1H), 5.52 (d, 1H), 5.06 (d, 2H), 4.64 (s, 1H), 4.43-4.21 (m, 1H), 4.08-3.72 (m, 2H), 1.39 (d, 3H)

Example 6 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-(difluoromethoxy)phenyl]-1H-1,2,4-triazol-5-yl}ethyl Acetate (XIV-A-3)

While cooling with ice, 55 µl (0.44 mmol) of (S)-(−)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 76 mg (0.44 mmol) of 2-difluoromethoxyphenylhydrazine (XIII) were added and then the mixture was stirred at RT overnight. The reaction mixture was then heated in the microwave at 100° C. for 3 h. A few drops of water were added to the reaction mixture, which was purified by chromatography (preparative HPLC, eluent: acetonitrile/water gradient, 0.1% formic acid). Lyophilization of the product-containing fractions gave 142 mg (58% of theory) of the title compound.

LC-MS (Method A): $R_t$=1.09 min; MS(ESIpos): m/z=617.1 [M+H]$^+$ $^1$H NMR (DMSO-d$_6$, 400 MHz): δ=7.83-6.82 (m, 10H), 5.69 (d, 1H), 5.09 (d, 2H), 4.30 (d, 1H), 4.07-3.77 (m, 2H), 1.77 (s, 3H), 1.53 (d, 3H)

b) 5-(4-Chlorophenyl)-2-({1-[2-(difluoromethoxy)phenyl]-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-3)

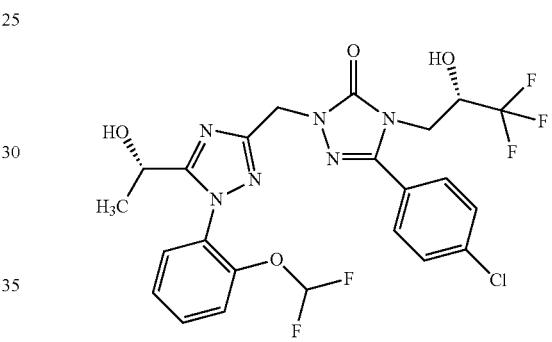

A mixture of 132 mg (0.21 mmol) of the compound from step a) and 214 µl (0.21 mmol) of 1 M sodium hydroxide solution in 1.3 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 117 mg (95% of theory) of the title compound.

LC-MS (Method A): $R_t$=0.99 min; MS(ESIpos): m/z=575.3 [M+H]$^+$ $^1$H NMR (DMSO-d$_6$, 400 MHz): δ=7.75 (d, 2H), 7.67-7.54 (m, 4H), 7.45-6.97 (m, 3H), 6.89 (d, 1H), 5.48 (d, 1H), 5.19-4.94 (m, 2H), 4.61 (quin, 1H), 4.30 (d, 1H), 4.09-3.76 (m, 2H), 1.39 (d, 3H)

Example 7 a) (1R)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-(difluoromethoxy)phenyl]-1H-1,2,4-triazol-5-yl}ethyl Acetate (XIV-B-3)

While cooling with ice, 73 µl (0.58 mmol) of (R)-(−)-2-acetoxypropionyl chloride (XII-B) were added dropwise to a mixture of 200 mg (0.53 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI)

and 276 µl (1.58 mmol) of DIPEA in 2 ml of THF. After 30 min at 0° C., 101 mg (0.58 mmol) of 2-difluoromethoxyphenylhydrazine (XIII) were added and then the mixture was stirred at RT overnight. The reaction mixture was then heated in the microwave at 150° C. for 3 h. A few drops of water were added to the reaction mixture, which was purified by chromatography (preparative HPLC, eluent: acetonitrile/water gradient, 0.1% formic acid). Lyophilization of the product-containing fractions gave 202 mg (62% of theory) of the title compound.

LC-MS (Method A): $R_t$=1.09 min; MS(ESIpos): m/z=617.3 [M+H]$^+$ $^1$H NMR (DMSO-$d_6$, 400 MHz): δ=7.89-6.81 (m, 10H), 5.79-5.59 (m, 1H), 5.09 (d, 2H), 4.35-4.22 (m, 1H), 4.09-3.78 (m, 2H), 1.76 (s, 3H), 1.53 (d, 3H)

b) 5-(4-Chlorophenyl)-2-({1-[2-(difluoromethoxy)phenyl]-5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-B-3)

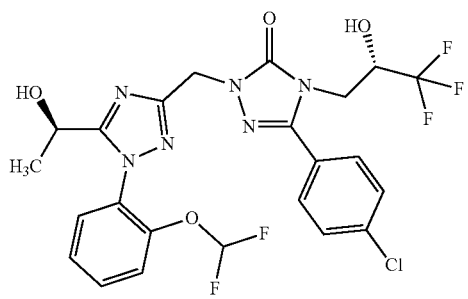 [SMILES: C[C@@H](O)c1nc(Cn2nc(-c3ccc(Cl)cc3)n(C[C@H](O)C(F)(F)F)c2=O)nn1-c1ccccc1OC(F)F]

A mixture of 192 mg (0.31 mmol) of the compound from step a) and 310 µl (0.31 mmol) of 1 M sodium hydroxide solution in 1.9 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 172 mg (96% of theory) of the title compound.

LC-MS (Method A): $R_t$=0.99 min; MS(ESIpos): m/z=575.3 [M+H]$^+$ $^1$H NMR (DMSO-$d_6$, 400 MHz): δ=7.75 (d, 2H), 7.68-7.53 (m, 4H), 7.46-6.96 (m, 3H), 6.91 (d, 1H), 5.48 (d, 1H), 5.06 (s, 2H), 4.61 (t, 1H), 4.30 (d, 1H), 4.07-3.75 (m, 1H), 1.39 (d, 1H)

Example 8 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-chloro-4-(trifluoromethyl)phenyl]-1H-1,2,4-triazol-5-yl}ethyl Acetate (XIV-A-4)

While cooling with ice, 55 µl (0.44 mmol) of (S)-(-)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 91 mg (0.44 mmol) of 2-chloro-4-(trifluoromethyl)phenylhydrazine (XIII) were added and the mixture was stirred at RT for 1 h. The reaction mixture was then heated in the microwave at 100° C. for 3 h. A few drops of water were added to the reaction mixture, which was purified by chromatography (preparative HPLC, eluent: acetonitrile/water gradient, 0.1% formic acid). Lyophilization of the product-containing fractions gave 111 mg (43% of theory) of the title compound.

LC-MS (Method A): $R_t$=1.21 min; MS(ESIpos): m/z=653.1 [M+H]$^+$ $^1$H NMR (DMSO-$d_6$, 400 MHz): δ=8.25 (s, 1H), 8.06-7.87 (m, 2H), 7.81-7.54 (m, 4H), 6.89 (d, 1H), 5.75 (s, 1H), 5.12 (d, 2H), 4.29 (d, 1H), 4.07-3.77 (m, 2H), 1.76 (s, 3H), 1.55 (d, 3H)

b) 5-(4-Chlorophenyl)-2-({1-[2-chloro-4-(trifluoromethyl)phenyl]-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-4)

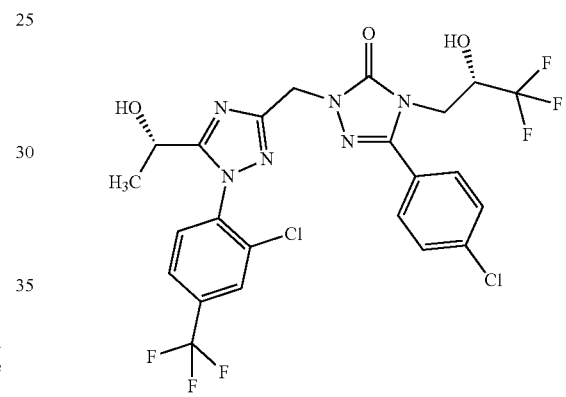

A mixture of 104 mg (0.16 mmol) of the compound from step a) and 160 µl (0.16 mmol) of 1 M sodium hydroxide solution in 1 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 94 mg (96% of theory) of the title compound.

LC-MS (Method A): $R_t$=1.06 min; MS(ESIpos): m/z=611.1 [M+H]$^+$ $^1$H NMR (DMSO-$d_6$, 400 MHz): δ=8.18 (s, 1H), 7.99-7.82 (m, 2H), 7.75 (d, 2H), 7.62 (d, 2H), 6.89 (d, 1H), 5.54 (d, 1H), 5.08 (d, 2H), 4.71 (t, 1H), 4.29 (d, 1H), 4.11-3.77 (m, 2H), 1.41 (d, 3H)

Example 9 a) (1S)-1-[1-(2-Chloro-6-fluorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]ethyl Acetate (XIV-A-5)

While cooling with ice, 55 µl (0.44 mmol) of (S)-(-)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 70 mg (0.44 mmol) of (2-chloro-6-fluorophenyl)hydrazine (XIII) were added and the mixture was stirred at RT for 1 h. The reaction mixture was then heated in the microwave at 100° C. for 3 h. A few drops of water were added to the reaction mixture, which was purified by chromatography (preparative HPLC, eluent: acetonitrile/water gradient, 0.1% formic acid). Lyophilization of the product-containing fractions gave 139 mg (58% of theory) of the title compound as an atropisomer mixture.

LC-MS (Method A): R$_t$=1.10 min; MS(ESIpos): m/z=603.1 [M+H]$^+$ $^1$H NMR (DMSO-d$_6$, 400 MHz): δ=7.82-7.50 (m, 7H), 6.89 (d, 1H), 5.73 (d, 1H), 5.25-5.04 (m, 2H), 4.43-4.19 (m, 1H), 4.10-3.78 (m, 2H), 1.79 (s, 3H), 1.54 (m, 3H)

b) 2-({1-(2-Chloro-6-fluorophenyl)-5-[(1S)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (I-A-5)

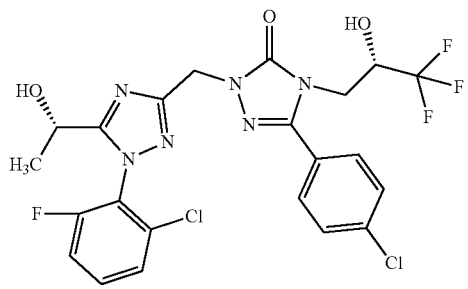 [SMILES: C[C@H](O)c1nc(Cn2nc(-c3ccc(Cl)cc3)n(C[C@H](O)C(F)(F)F)c2=O)nn1-c1c(F)cccc1Cl]

A mixture of 129 mg (0.21 mmol) of the compound from step a) and 214 µl (0.21 mmol) of 1 M sodium hydroxide solution in 1.3 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 114 mg (95% of theory) of the title compound as an atropisomer mixture.

LC-MS (Method A): R$_t$=0.99 min; MS(ESIpos): m/z=561.3 [M+H]$^+$ $^1$H NMR (DMSO-d$_6$, 400 MHz): δ=7.79-7.46 (m, 7H), 6.89 (d, 1H), 5.60 (dd, 1H), 5.22-4.97 (m, 2H), 4.84-4.55 (m, 1H), 4.29 (d, 1H), 4.08-3.73 (m, 2H), 1.44-1.33 (m, 3H)

Example 10 a) (1R)-1-[1-(2-Chloro-6-fluorophenyl)-3-({3-(4-chlorophenyl)-5-oxo-4-[(2S)-3,3,3-trifluoro-2-hydroxypropyl]-4,5-dihydro-H-1,2,4-triazol-1-yl}methyl)-1H-1,2,4-triazol-5-yl]ethyl Acetate (XIV-B-5)

While cooling with ice, 55 µl (0.44 mmol) of (R)-(−)-2-acetoxypropionyl chloride (XII-B) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 70 mg (0.44 mmol) of 2-chloro-6-fluorophenylhydrazine (XIII) were added and then the mixture was stirred at RT overnight. The reaction mixture was then heated in the microwave at 150° C. for 1 h. A few drops of water were added to the reaction mixture, which was purified by chromatography (preparative HPLC, eluent: acetonitrile/water gradient, 0.1% formic acid). Lyophilization of the product-containing fractions gave 162 mg (68% of theory) of the title compound as a mixture of atropisomers.

LC-MS (Method A): R$_t$=1.10 min; MS(ESIpos): m/z=603.3 [M+H]$^+$ $^1$H NMR (DMSO-d$_6$, 400 MHz): δ=7.83-7.49 (m, 7H), 6.96-6.84 (m, 1H), 5.73 (d, 1H), 5.13 (d, 2H), 4.29 (br. s., 1H), 4.09-3.76 (m, 2H), 1.79 (d, 3H), 1.54 (dd, 3H)

b) 2-({1-(2-Chloro-6-fluorophenyl)-5-[(1R)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (I-B-5)

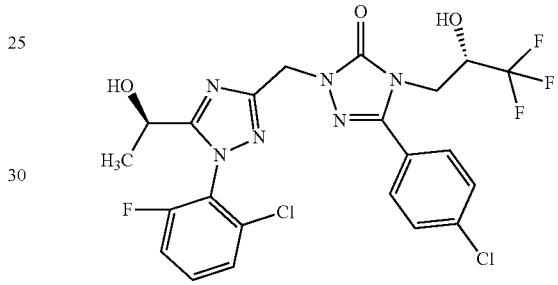

A mixture of 152 mg (0.25 mmol) of the compound from step a) and 250 µl (0.25 mmol) of 1 M sodium hydroxide solution in 1.5 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 137 mg (95% of theory) of the title compound as an atropisomer mixture.

LC-MS (Method A): R$_t$=0.99 min; MS(ESIpos): m/z=561.2 [M+H]$^+$ $^1$H NMR (DMSO-d$_6$, 400 MHz): δ=7.83-7.43 (m, 7H), 6.90 (d, 1H), 5.60 (dd, 1H), 5.26-4.92 (m, 2H), 4.84-4.54 (m, 1H), 4.29 (d, 1H), 4.11-3.72 (m, 2H), 1.44-1.33 (m, 3H)

Example 11 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[4-fluoro-2-(trifluoromethyl)phenyl]-1H-1,2,4-triazol-5-yl}ethyl Acetate (XIV-A-6)

While cooling with ice, 55 µl (0.44 mmol) of (S)-(−)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 100 mg (0.44 mmol) of 4-fluoro-2-(trifluoromethyl)phenylhydrazine (XIII) hydrochloride were added and the mixture was stirred at RT for 3 h. The reaction mixture was then heated in the microwave at 150° C. for 3 h. A few drops of water were added to the reaction mixture, which was purified by chromatography (preparative HPLC, eluent: acetonitrile/water gradient, 0.1% formic acid). Lyophilization of the product-containing fractions gave 129 mg (51% of theory) of the title compound.

LC-MS (Method A): $R_t$=1.14 min; MS(ESIpos): m/z=637.3 [M+H]$^+$ $^1$H NMR (DMSO-d$_6$, 400 MHz): δ=8.05-7.54 (m, 7H), 6.88 (d, 1H), 5.75 (s, 1H), 5.09 (d, 2H), 4.38-4.18 (m, 1H), 4.08-3.74 (m, 2H), 1.78 (br. s., 3H), 1.51 (d, 3H)

b) 5-(4-Chlorophenyl)-2-({1-[4-fluoro-2-(trifluoromethyl)phenyl]-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-6)

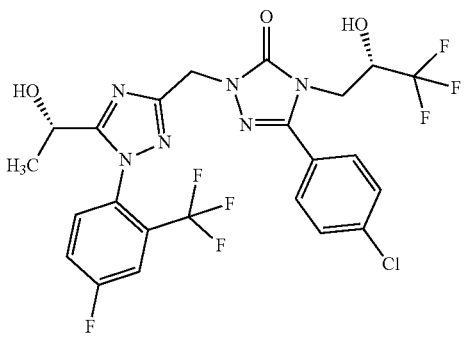

A mixture of 119 mg (0.19 mmol) of the compound from step a) and 187 µl (0.19 mmol) of 1 M sodium hydroxide solution in 1.1 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 110 mg (quant.) of the title compound.

LC-MS (Method A): $R_t$=1.03 min; MS(ESIpos): m/z=595.1 [M+H]$^+$ $^1$H NMR (DMSO-d$_6$, 400 MHz): δ=7.96-7.87 (m, 1H), 7.83-7.55 (m, 6H), 6.89 (d, 1H), 5.50 (d, 1H), 5.16-4.94 (m, 2H), 4.69-4.50 (m, 1H), 4.28 (br. s., 1H), 4.07-3.75 (m, 2H), 1.37 (d, 3H)

Example 12 a) (1S)-1-[1-(2-Chloro-4-fluorophenyl)-3-({3-(4-chlorophenyl)-5-oxo-4-[(2S)-3,3,3-trifluoro-2-hydroxypropyl]-4,5-dihydro-H-1,2,4-triazol-1-yl}methyl)-1H-1,2,4-triazol-5-yl]ethyl Acetate (XIV-A-7)

While cooling with ice, 55 µl (0.44 mmol) of (S)-(−)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 85 mg (0.44 mmol) of 2-chloro-4-fluorophenylhydrazine hydrochloride (XIII) were added and the mixture was stirred at RT for 2 h. The reaction mixture was then heated in the microwave at 150° C. for 3 h. A few drops of water were added to the reaction mixture, which was purified by chromatography (preparative HPLC, eluent: acetonitrile/water gradient, 0.1% formic acid). Lyophilization of the product-containing fractions gave 157 mg (66% of theory) of the title compound.

LC-MS (Method A): $R_t$=1.07 min; MS(ESIpos): m/z=603.0 [M+H]$^+$ $^1$H NMR (DMSO-d$_6$, 400 MHz): δ=7.90-7.33 (m, 7H), 6.88 (d, 1H), 5.96-5.47 (m, 1H), 5.10 (d, 2H), 4.29 (d, 1H), 4.11-3.74 (m, 2H), 1.82 (br. s., 3H), 1.53 (d, 3H)

b) 2-({1-(2-Chloro-4-fluorophenyl)-5-[(1S)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1-1,2,4-triazol-3-one (I-A-7)

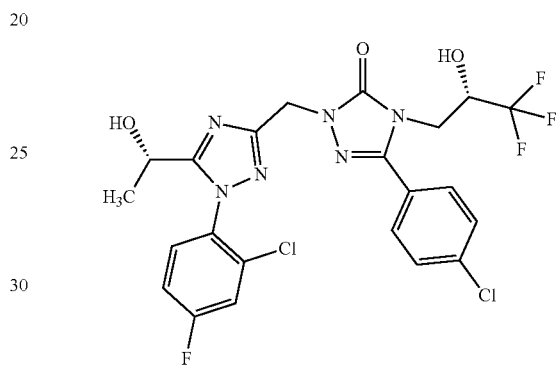

A mixture of 152 mg (0.25 mmol) of the compound from step A) and 252 µl (0.25 mmol) of 1 M sodium hydroxide solution in 1.5 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 140 mg (quant.) of the title compound.

LC-MS (Method A): $R_t$=1.00 min; MS(ESIpos): m/z=561.2 [M+H]$^+$ $^1$H NMR (DMSO-d$_6$, 400 MHz): δ=7.84-7.54 (m, 6H), 7.42 (td, 1H), 6.89 (d, 1H), 5.51 (d, 1H), 5.06 (d, 2H), 4.72-4.51 (m, 1H), 4.40-4.19 (m, 1H), 4.10-3.74 (m, 2H), 1.38 (d, 3H)

Example 13 a) (1R)-1-[1-(2-Chloro-4-fluorophenyl)-3-({3-(4-chlorophenyl)-5-oxo-4-[(2S)-3,3,3-trifluoro-2-hydroxypropyl]-4,5-dihydro-H-1,2,4-triazol-1-yl}methyl)-1H-1,2,4-triazol-5-yl]ethyl Acetate (XIV-B-7)

While cooling with ice, 109 mg (0.73 mmol) of (R)-(−)-2-acetoxypropionyl chloride (XII-B) were added dropwise to a mixture of 250 mg (0.66 mmol) of methyl 5-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 345 µl (1.98 mmol) of DIPEA in 2 ml of THF. After 30 min at 0° C., 143 mg (0.73 mmol) of 2-chloro-4-fluorophenylhydrazine hydrochloride (XIII) were added and then the mixture was stirred at RT overnight. The reaction mixture was subsequently heated in the microwave at 120° C. for 3 h and purified by chromatography (preparative HPLC, eluent: acetonitrile/water gradient, 0.1% formic acid). Lyophilization of the product-containing fractions gave 177 mg (44% of theory) of the title compound.

LC-MS (Method A): $R_t$=1.10 min; MS(ESIpos): m/z=603.2 [M+H]$^+$ $^1$H NMR (DMSO-d$_6$, 400 MHz): δ=7.96-7.31 (m, 7H), 6.89 (d, 1H), 5.75 (s, 1H), 5.26-4.96 (m, 2H), 4.29 (br. s., 1H), 4.10-3.76 (m, 2H), 1.82 (br. s., 3H), 1.53 (d, 3H)

b) 2-({1-(2-Chloro-4-fluorophenyl)-5-[(1R)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (I-B-7)

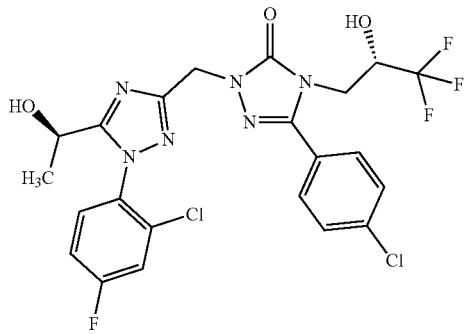 [SMILES: C[C@@H](O)c1nc(Cn2nc(-c3ccc(Cl)cc3)n(C[C@H](O)C(F)(F)F)c2=O)nn1-c1ccc(F)cc1Cl]

A mixture of 165 mg (0.27 mmol) of the compound from step a) and 275 µl (0.27 mmol) of 1 M sodium hydroxide solution in 3.3 ml of methanol was stirred at RT for 30 min. A few drops of 50% aqueous formic acid were added to the reaction mixture, which was purified by means of preparative HPLC (preparative HPLC, eluent: acetonitrile/water gradient, 0.1% formic acid). Lyophilization of the product-containing fractions gave 144 mg (93% of theory) of the title compound.

LC-MS (Method A): $R_t$=0.96 min; MS(ESIpos): m/z=561.00 [M+H]$^+$ $^1$H NMR (DMSO-d$_6$, 400 MHz): δ=7.89-7.54 (m, 6H), 7.42 (td, 1H), 6.90 (d, 1H), 5.51 (d, 1H), 5.06 (s, 2H), 4.72-4.51 (m, 1H), 4.30 (d, 1H), 4.12-3.75 (m, 2H), 1.38 (d, 3H)

Example 14 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[4-chloro-2-(trifluoromethyl)phenyl]-1H-1,2,4-triazol-5-yl}ethyl Acetate (XIV-A-8)

While cooling with ice, 55 µl (0.44 mmol) of (S)-(-)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 107 mg (0.44 mmol) of 4-chloro-2-(trifluoromethyl)phenylhydrazine hydrochloride (XIII) were added and the mixture was stirred at RT for 3 h. The reaction mixture was then heated in the microwave at 150° C. for 3 h. A few drops of water were added to the reaction mixture, which was purified by chromatography (preparative HPLC, eluent: acetonitrile/water gradient, 0.1% formic acid). Lyophilization of the product-containing fractions gave 125 mg (48% of theory) of the title compound.

LC-MS (Method A): $R_t$=1.19 min; MS(ESIpos): m/z=653.3 [M+H]$^+$ $^1$H NMR (DMSO-d$_6$, 400 MHz): δ=8.23-7.54 (m, 7H), 6.88 (d, 1H), 5.75 (s, 1H), 5.22-4.96 (m, 2H), 4.28 (d, 1H), 4.08-3.72 (m, 2H), 1.78 (br. s., 3H), 1.51 (d, 3H)

b) 5-(4-Chlorophenyl)-2-({1-[4-chloro-2-(trifluoromethyl)phenyl]-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-8)

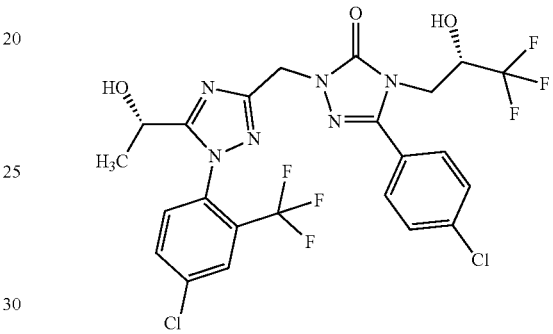

A mixture of 129 mg (0.2 mmol) of the compound from step a) and 200 µl (0.2 mmol) of 1 M sodium hydroxide solution in 1.2 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 109 mg (90% of theory) of the title compound.

LC-MS (Method A): $R_t$=1.08 min; MS(ESIpos): m/z=611.0 [M+H]$^+$ $^1$H NMR (DMSO-d$_6$, 400 MHz): δ=8.15-7.92 (m, 2H), 7.82-7.56 (m, 5H), 6.89 (d, 1H), 5.51 (d, 1H), 5.18-4.96 (m, 2H), 4.64 (t, 1H), 4.29 (d, 1H), 4.10-3.73 (m, 2H), 1.37 (d, 3H)

Example 15 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-chloro-4-(trifluoromethoxy)phenyl]-1H-1,2,4-triazol-5-yl}ethyl Acetate (XIV-A-9)

While cooling with ice, 55 µl (0.44 mmol) of (S)-(-)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 1.5 ml of THF. After 30 min at 0° C., 107 mg (0.44 mmol) of 2-chloro-4-(trifluoromethoxy)phenylhydrazine (XIII) were added and then the mixture was stirred at RT overnight. The reaction mixture was then heated in the microwave at 100° C. for 3 h. A few drops of water were added to the reaction mixture, which was purified by chromatography (preparative HPLC, eluent: acetonitrile/water gradient, 0.1% formic acid). Lyophilization of the product-containing fractions gave 152 mg (57% of theory) of the title compound.

LC-MS (Method A): $R_t$=1.23 min; MS(ESIpos): m/z=669.1 [M+H]$^+$ $^1$H NMR (DMSO-d$_6$, 400 MHz): δ=8.01-7.53 (m, 7H), 6.89 (d, 1H), 5.92-5.60 (m, 1H), 5.11 (d, 2H), 4.39-4.19 (m, 1H), 4.09-3.77 (m, 2H), 1.77 (br. s., 3H), 1.54 (d, 3H)

b) 5-(4-Chlorophenyl)-2-({1-[2-chloro-4-(trifluoromethoxy)phenyl]-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-9)

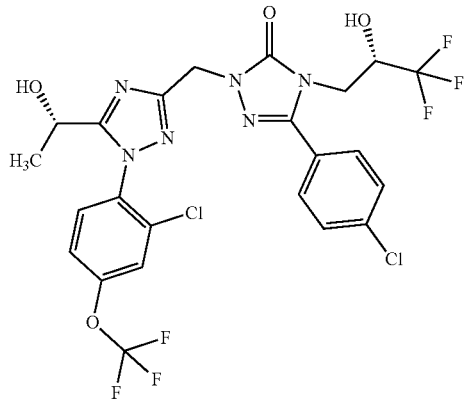 [SMILES: C[C@H](O)c1nc(Cn2nc(-c3ccc(Cl)cc3)n(C[C@H](O)C(F)(F)F)c2=O)nn1-c1ccc(OC(F)(F)F)cc1Cl]

A mixture of 141 mg (0.21 mmol) of the compound from step a) and 210 µl (0.21 mmol) of 1 M sodium hydroxide solution in 1.3 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 125 mg (94% of theory) of the title compound.

LC-MS (Method A): $R_t$=1.11 min; MS(ESIpos): m/z=627.3 [M+H]$^+$ $^1$H NMR (DMSO-d$_6$, 400 MHz): δ=7.87 (d, 1H), 7.82-7.71 (m, 4H), 7.67-7.51 (m, 4H), 6.89 (d, 1H), 5.54 (d, 1H), 5.07 (d, 2H), 4.75-4.58 (m, 1H), 4.39-4.17 (m, 1H), 4.08-3.74 (m, 2H), 1.40 (d, 3H)

Example 16 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2,6-dichlorophenyl]-1H-1,2,4-triazol-5-yl]ethyl Acetate (XIV-A-10)

While cooling with ice, 73 µl (0.58 mmol) of (S)-(−)-2-acetoxypropionyl chloride (XII-A) were added dropwise to a mixture of 200 mg (0.53 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 276 µl (1.58 mmol) of DIPEA in 2 ml of THF. After 1 h at 0° C., 124 mg (0.58 mmol) of 2,6-dichlorophenylhydrazine (XIII) hydrochloride were added and then the mixture was stirred at RT overnight. The reaction mixture was then heated in the microwave at 100° C. for 3 h. A few drops of water were added to the reaction mixture, which was purified by chromatography (preparative HPLC, eluent: acetonitrile/water gradient, 0.1% formic acid). Lyophilization of the product-containing fractions gave 124 mg (37% of theory) of the title compound.

LC-MS (Method A): $R_t$=1.08 min; MS(ESIpos): m/z=619.0 [M+H]$^+$ $^1$H NMR (DMSO-d$_6$, 400 MHz): δ=7.84-7.52 (m, 1H), 6.89 (d, 1H), 5.78 (d, 1H), 5.13 (d, 2H), 4.41-4.20 (m, 1H), 4.11-3.70 (m, 2H), 1.78 (s, 3H), 1.55 (d, 3H)

b) 5-(4-Chlorophenyl)-2-({1-(2,6-dichlorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-10)

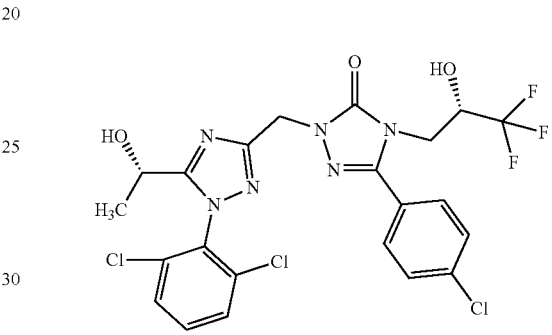

A mixture of 119 mg (0.19 mmol) of the compound from step a) and 190 µl (0.19 mmol) of 1 M aqueous sodium hydroxide solution in 2 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 110 mg (quant.) of the title compound.

LC-MS (Method A): $R_t$=1.00 min; MS(ESIpos): m/z=576.9 [M+H]$^+$ $^1$H NMR (DMSO-d$_6$, 400 MHz): δ=7.81-7.54 (m, 7H), 6.90 (d, 1H), 5.55 (d, 1H), 5.19-4.96 (m, 2H), 4.63 (t, 1H), 4.30 (d, 1H), 4.08-3.77 (m, 2H), 1.41 (d, 3H)

Example 17 a) (1R)-1-[3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(2,6-dichlorophenyl)-1H-1,2,4-triazol-5-yl]ethyl Acetate (XIV-B-10)

While cooling with ice, 73 µl (0.58 mmol) of (R)-(−)-2-acetoxypropionyl chloride (XII-B) were added dropwise to a mixture of 200 mg (0.53 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 276 µl (1.58 mmol) of DIPEA in 2 ml of THF. After 30 min at 0° C., 124 mg (0.58 mmol) of 2,6-dichlorophenylhydrazine (XIII) hydrochloride were added and then the mixture was stirred at RT overnight. The reaction mixture was then heated in the microwave at 150° C. for 3 h. A few drops of water were added to the reaction mixture, which was purified by chromatography (preparative HPLC, eluent:

acetonitrile/water gradient, 0.1% formic acid). Lyophilization of the product-containing fractions gave 151 mg (46% of theory) of the title compound.

LC-MS (Method A): $R_t$=1.12 min; MS(ESIpos): m/z=619.2 [M+H]$^+$ $^1$H NMR (DMSO-d$_6$, 400 MHz): δ=7.83-7.56 (m, 8H), 6.90 (d, 1H), 5.78 (d, 1H), 5.13 (d, 2H), 4.42-4.12 (m, 1H), 4.06-3.74 (m, 2H), 1.78 (s, 3H), 1.55 (d, 3H)

b) 5-(4-Chlorophenyl)-2-({1-(2,6-dichlorophenyl)-5-[(1R)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-B-10)

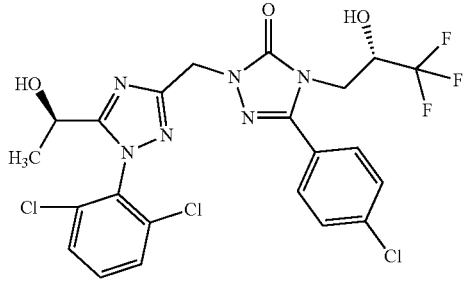 [SMILES: C[C@@H](O)c1nc(Cn2nc(-c3ccc(Cl)cc3)n(C[C@H](O)C(F)(F)F)c2=O)nn1-c1c(Cl)cccc1Cl]

A mixture of 141 mg (0.23 mmol) of the compound from step a) and 230 µl (0.23 mmol) of 1 M sodium hydroxide solution in 2.4 ml of methanol was stirred at 0° C. for 2 min and at RT for 90 min. 0.5 g of activated ion exchanger (Dowex 50WX8, 200-400 mesh) was added and the mixture was stirred at RT for 30 min. The ion exchanger was then filtered off, and washed with methanol. The filtrate was concentrated and the residue was dried under reduced pressure. This gave 128 mg (97% of theory) of the title compound.

LC-MS (Method A): $R_t$=1.01 min; MS(ESIpos): m/z=577.2 [M+H]$^+$ $^1$H NMR (DMSO-d$_6$, 400 MHz): δ=7.78-7.57 (m, 7H), 6.90 (d, 1H), 5.55 (d, 1H), 5.08 (d, 2H), 4.63 (t, 1H), 4.40-4.19 (m, 1H), 4.12-3.76 (m, 2H), 1.41 (d, 3H)

Example 18 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethoxy)phenyl]-1H-1,2,4-triazol-5-yl}ethyl Acetate (XIV-A-11)

While cooling with ice, 55 µl (0.44 mmol) of (S)-(−)-2-acetoxypropionyl chloride (XII-A) were added dropwise to a mixture of 150 mg (0.40 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 207 µl (1.19 mmol) of DIPEA in 3 ml of THF. After 30 min at 0° C., 143 mg (0.73 mmol) of 2-trifluoromethoxyphenylhydrazine (XIII) hydrochloride were added and then the mixture was stirred at RT overnight. The reaction mixture was subsequently heated in the microwave at 120° C. for 3 h and purified by chromatography (preparative HPLC, eluent: acetonitrile/water gradient, 0.1% formic acid). Lyophilization of the product-containing fractions gave 141 mg (56% of theory) of the title compound.

LC-MS (Method A): $R_t$=1.14 min; MS(ESIpos): m/z=635.3 [M+H]$^+$ b) 5-(4-Chlorophenyl)-2-({5-[(1S)-1-hydroxyethyl]-1-[2-(trifluoromethoxy)phenyl]-1H-1,2,4-triazol-3-yl}methyl)-4-[(2S)-3,3,3-trifluoro-2-hydroxypropyl]-2,4-dihydro-3H-1,2,4-triazol-3-one (I-A-11)

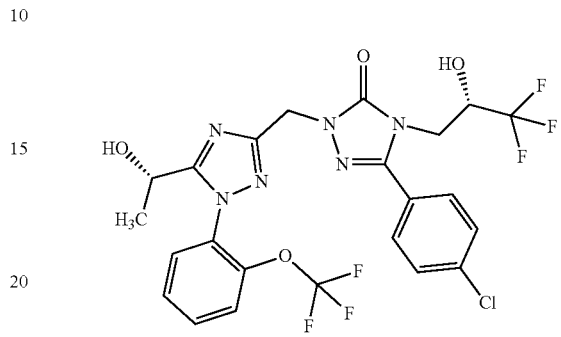

A mixture of 140 mg (0.22 mmol) of the compound from step a) and 220 µl (0.22 mmol) of 1 M sodium hydroxide solution in 2 ml of methanol was stirred at RT for 60 min. Subsequently, 17 µl of 50% formic acid were added and the mixture was purified by chromatography (preparative HPLC, eluent: acetonitrile/water gradient, 0.1% formic acid). Lyophilization of the product-containing fractions gave 123 mg (94% of theory) of the title compound.

LC-MS (Method A): $R_t$=1.04 min; MS(ESIpos): m/z=593.3 [M+H]$^+$ $^1$H NMR (DMSO-d$_6$, 400 MHz): δ=7.77-7.51 (m, 8H), 6.89 (d, 1H), 5.54 (d, 1H), 5.06 (d, 2H), 4.63 (t, 1H), 4.41-4.18 (m, 1H), 4.07-3.77 (m, 2H), 1.40 (d, 3H)

Example 19 a) (1R)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethoxy)phenyl]-1H-1,2,4-triazol-5-yl}ethyl Acetate (XIV-B-11)

While cooling with ice, 109 mg (0.73 mmol) of (R)-(−)-2-acetoxypropionyl chloride (XII-B) were added dropwise to a mixture of 250 mg (0.66 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 345 µl (1.98 mmol) of DIPEA in 5 ml of THF. After 30 min at 0° C., 166 mg (0.73 mmol) of 2-trifluoromethoxyphenylhydrazine (XIII) hydrochloride were added and then the mixture was stirred at RT overnight. The reaction mixture was subsequently heated in the microwave at 120° C. for 3 h and purified by chromatography (preparative HPLC, eluent: acetonitrile/water gradient, 0.1% formic acid). Lyophilization of the product-containing fractions gave 167 mg (39% of theory) of the title compound.

LC-MS (Method A): $R_t$=1.13 min; MS(ESIpos): m/z=635.3 [M+H]$^+$ $^1$H NMR (DMSO-d$_6$, 400 MHz): δ=7.83-7.48 (m, 8H), 6.89 (d, 1H), 5.75 (d, 1H), 5.10 (d, 2H), 4.41-4.20 (m, 1H), 4.11-3.76 (m, 2H), 1.75 (s, 3H), 1.53 (d, 3H)

b) 5-(4-Chlorophenyl)-2-({5-[(1R)-1-hydroxyethyl]-1-[2-(trifluoromethoxy) phenyl]-1H-1,2,4-triazol-3-yl}methyl)-4-[(2S)-3,3,3-trifluoro-2-hydroxypropyl]-2,4-dihydro-3H-1,2,4-triazol-3-one (I-B-11)

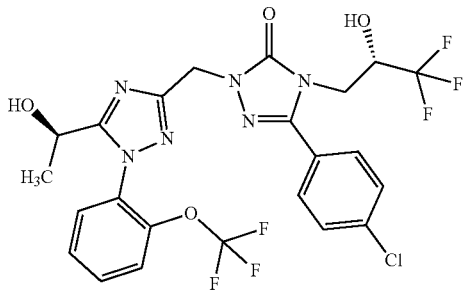 [SMILES: C[C@@H](O)c1nc(Cn2nc(-c3ccc(Cl)cc3)n(C[C@H](O)C(F)(F)F)c2=O)nn1-c1ccccc1OC(F)(F)F]

A mixture of 158 mg (0.25 mmol) of the compound from step a) and 250 µl (0.25 mmol) of 1 M sodium hydroxide solution in 3 ml of methanol was stirred at 0° C. for 2 min and at RT for 90 min. Subsequently, 19 µl of 50% formic acid were added and the mixture was purified by chromatography (preparative HPLC, eluent: acetonitrile/water gradient, 0.1% formic acid). Lyophilization of the product-containing fractions gave 139 mg (94% of theory) of the title compound.

LC-MS (Method A): $R_t$=1.00 min; MS(ESIpos): m/z=593.00 [M+H]$^+$ $^1$H NMR (DMSO-d$_6$, 400 MHz): δ=7.80-7.51 (m, 8H), 6.90 (d, 1H), 5.54 (d, 1H), 5.06 (s, 2H), 4.63 (t, 1H), 4.39-4.21 (m, 1H), 4.08-3.76 (m, 1H), 1.40 (d, 1H)

Example 20 a) (1S)-1-[1-(2,6-Difluorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]ethyl Acetate (XIV-A-12)

While cooling with ice, 37 µl (0.29 mmol) of (S)-(−)-2-acetoxypropionyl chloride (XII-A) were added dropwise to a mixture of 100 mg (0.26 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 138 µl (0.79 mmol) of DIPEA in 2 ml of THF. After 30 min at 0° C., 53 mg (0.29 mmol) of 2,6-difluorophenylhydrazine (XIII) were added and then the mixture was stirred at RT overnight. The reaction mixture was subsequently heated in the microwave at 120° C. for 3 h and purified by chromatography (preparative HPLC, eluent: acetonitrile/water gradient, 0.1% formic acid). Lyophilization of the product-containing fractions gave 130 mg (83% of theory) of the title compound.

LC-MS (Method A): $R_t$=1.07 min; MS(ESIpos): m/z=587.1 [M+H]$^+$ $^1$H NMR (DMSO-d$_6$, 400 MHz): δ=7.91-7.31 (m, 7H), 6.89 (d, 1H), 5.74 (d, 1H), 5.12 (d, 2H), 4.40-4.18 (m, 1H), 4.09-3.74 (m, 2H), 1.80 (s, 3H), 1.53 (d, 3H)

b) 5-(4-Chlorophenyl)-2-({1-(2,6-difluorophenyl)-5-[(1S)-1-hydroxyethyl]-1H-1,2,4-triazol-3-yl}methyl)-4-[(2S)-3,3,3-trifluoro-2-hydroxypropyl]-2,4-dihydro-3H-1,2,4-triazol-3-one (I-A-12)

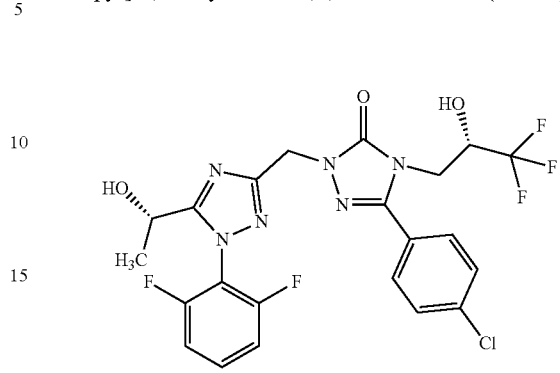

A mixture of 120 mg (0.20 mmol) of the compound from step a) and 200 µl (0.20 mmol) of 1 M sodium hydroxide solution in 2 ml of methanol was stirred at RT for 60 min. Subsequently, 16 µl of 50% formic acid were added and the mixture was purified by chromatography (preparative HPLC, eluent: acetonitrile/water gradient, 0.1% formic acid). Lyophilization of the product-containing fractions gave 110 mg (99% of theory) of the title compound.

LC-MS (Method A): $R_t$=0.97 min; MS(ESIpos): m/z=545.2 [M+H]$^+$ $^1$H NMR (DMSO-d$_6$, 400 MHz): δ=7.86-7.57 (m, 5H), 7.38 (s, 2H), 6.89 (d, 1H), 5.63 (d, 1H), 5.08 (s, 2H), 4.74 (t, 1H), 4.30 (d, 1H), 4.11-3.71 (m, 2H), 1.39 (d, 3H)

Example 21 a) (1S)-1-{3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[4-chloro-2-(trifluoromethoxy)phenyl]-1H-1,2,4-triazol-5-yl}ethyl Acetate (XIV-A-13)

While cooling with ice, 37 µl (0.29 mmol) of (S)-(−)-2-acetoxypropionyl chloride (XII-A) were added dropwise to a mixture of 100 mg (0.26 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 138 µl (0.79 mmol) of DIPEA in 2 ml of THF. After 30 min at 0° C., 53 mg (0.29 mmol) of 4-chloro-2-(trifluoromethoxy)phenylhydrazine were added and then the mixture was stirred at RT overnight. The reaction mixture was subsequently heated in the microwave at 120° C. for 3 h and purified by chromatography (preparative HPLC, eluent: acetonitrile/water gradient, 0.1% formic acid). Lyophilization of the product-containing fractions gave 76 mg (43% of theory) of the title compound.

LC-MS (Method A): $R_t$=1.17 min; MS(ESIpos): m/z=669.1 [M+H]$^+$ $^1$H NMR (DMSO-d$_6$, 400 MHz): δ=8.01-7.53 (m, 7H), 6.88 (d, 1H), 5.74 (d, 1H), 5.10 (d, 2H), 4.29 (d, 1H), 4.10-3.75 (m, 2H), 1.79 (s, 3H), 1.53 (d, 3H)

b) 5-(4-Chlorophenyl)-2-({1-[4-chloro-2-(trifluoromethoxy)phenyl]-5-[(1S)-1-hydroxyethyl]-1H-1,2,4-triazol-3-yl}methyl)-4-methyl)-4-[(2S)-3,3,3-trifluoro-2-hydroxypropyl]-2,4-dihydro-3H-1,2,4-triazol-3-one (I-A-13)

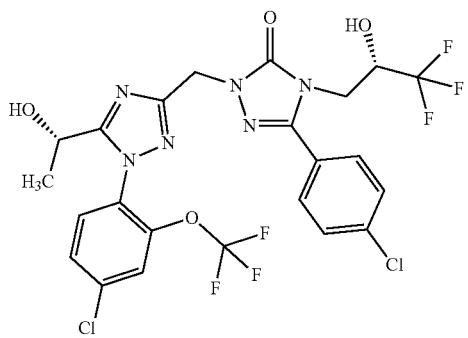 [SMILES: C[C@H](O)c1nc(Cn2nc(-c3ccc(Cl)cc3)n(C[C@H](O)C(F)(F)F)c2=O)nn1-c1ccc(Cl)cc1OC(F)(F)F]

A mixture of 70 mg (0.10 mmol) of the compound from step a) and 105 μl (0.10 mmol) of 1 M sodium hydroxide solution in 1 ml of methanol was stirred at RT for 30 min. Subsequently, 8 μl of 50% formic acid were added and the mixture was purified by chromatography (preparative HPLC, eluent: acetonitrile/water gradient, 0.1% formic acid). Lyophilization of the product-containing fractions gave 59 mg (90% of theory) of the title compound.

LC-MS (Method A): $R_t$=1.12 min; MS(ESIpos): m/z=627.3 [M+H]$^+$ $^1$H NMR (DMSO-$d_6$, 400 MHz): δ=7.87-7.56 (m, 7H), 6.92-6.85 (m, 1H), 5.55 (d, 1H), 5.20-4.96 (m, 2H), 4.68 (t, 1H), 4.29 (d, 1H), 4.10-3.73 (m, 1H), 1.40 (d, 1H)

Example 22 a) (1S)-1-[1-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-5-yl]ethyl Acetate (XIV-A-14)

While cooling with ice, 5.2 ml (41.0 mmol) of (S)-(−)-2-acetoxypropionyl chloride (XII-A) were added dropwise to a mixture of 14.1 g (37.3 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 32.5 ml (41.0 mmol) of DIPEA in 303 ml of THF. After 1.5 h at 0° C., 7.35 mg (0.44 mmol) of 2-chlorophenylhydrazine (XIII) hydrochloride were added and the mixture was stirred at RT for 1.5 h. The reaction mixture was then heated in the microwave at 100° C. for 10 h. The reaction mixture was then admixed with water and ethyl acetate and stirred vigorously. The phases were separated. The aqueous phase was extracted with ethyl acetate. The organic phase was washed with saturated aqueous ammonium chloride solution, dried over magnesium sulphate and concentrated under reduced pressure. The residue was purified by chromatography (silica gel, eluent: cyclohexane/ethyl acetate gradient). Concentration of the product-containing fractions by rotary evaporation gave 10.4 mg (47% of theory) of the title compound.

LC-MS (Method A): $R_t$=1.09 min; MS(ESIpos): m/z=585.2 [M+H]$^+$ $^1$H NMR (DMSO-$d_6$, 400 MHz): δ=7.84-7.49 (m, 8H), 6.89 (d, 1H), 5.75 (br. s, 1H), 5.22-5.00 (m, 2H), 4.4-3.70 (m, 3H), 1.77 (br s, 3H), 1.58-1.44 (m, 3H)

b) 2-({1-(2-Chlorophenyl)-5-[(1S)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (I-A-14)

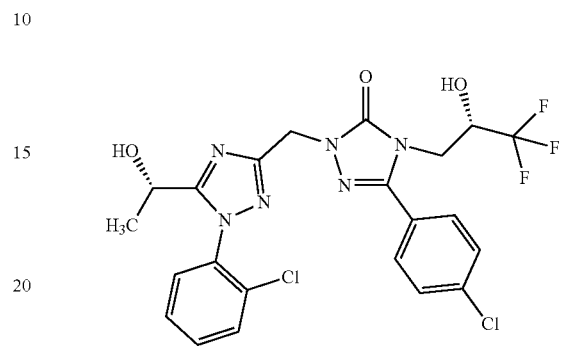

A mixture of 10.4 g (17.7 mmol) of the compound from step a) and 2.84 g (35.5 mmol) of a 50% aqueous sodium hydroxide solution in 110 ml of methanol/water mixture (10:1) was stirred at 0° C. for 2 min and at RT for 1 h. The mixture was added to water and adjusted to pH 7 with a 1 N hydrochloric acid solution. The aqueous phase was extracted with MTBE. The organic phase was washed with saturated aqueous sodium chloride solution, dried over magnesium sulphate and concentrated under reduced pressure. This gave 10.6 g (quant.) of the title compound.

LC-MS (Method 2): $R_t$=1.75 min; MS(ESIpos): m/z=543.1 [M+H]$^+$ $^1$H NMR (DMSO-$d_6$, 400 MHz): δ=7.94-7.35 (m, 8H), 6.89 (d, 1H), 5.50 (d, 1H), 5.07 (d, 2H), 4.69-3.70 (m, 4H), 1.38 (d, 3H)

Example 23 a) (1R)-1-[1-(2-Chlorophenyl)-3-({3-(4-chlorophenyl)-5-oxo-4-[(2R)-3,3,3-trifluoro-2-hydroxypropyl]-4,5-dihydro-1H-1,2,4-triazol-1-yl}methyl)-1H-1,2,4-triazol-5-yl]ethyl Acetate (XIV-B-14)

1.09 g (7.3 mmol) of (R)-(−)-2-acetoxypropionyl chloride (XII-B) were added dropwise to a mixture of 2.5 g (6.6 mmol) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (XI) and 4.6 ml (26.4 mmol) of DIPEA in 65 ml of dioxane. After 30 min at RT, 1.3 g (7.3 mmol) of 2-chlorophenylhydrazine (XIII) were added. The reaction mixture was stirred at RT for 2 h and heated under reflux overnight. The reaction mixture was concentrated and purified by chromatography (silica gel, eluent: cyclohexane/ethyl acetate gradient). Concentration of the product-containing fractions by rotary evaporation gave 2.87 g (74% of theory) of the title compound.

LC-MS (Method A): $R_t$=1.12 min; MS(ESIpos): m/z=585.2 [M+H]$^+$ $^1$H NMR (DMSO-$d_6$, 400 MHz): δ=7.90-7.45 (m, 8H), 6.89 (d, 1H), 5.86-5.53 (m, 1H), 5.11 (d, 2H), 4.37-4.22 (m, 1H), 4.11-3.78 (m, 2H), 1.77 (br s, 3H), 1.53 (d, 3H)

b) 2-({1-(2-Chlorophenyl)-5-[(1R)-1-hydroxyethyl]-1H-1,2,4-triazol-3-yl}methyl)-5-(4-chlorophenyl)-4-[(2S)-3,3,3-trifluoro-2-hydroxypropyl]-2,4-dihydro-3H-1,2,4-triazol-3-one (I-B-14)

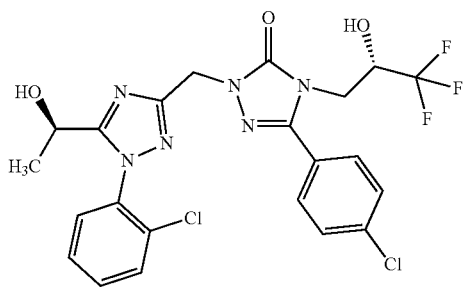 [SMILES: C[C@@H](O)c1nc(Cn2nc(-c3ccc(Cl)cc3)n(C[C@H](O)C(F)(F)F)c2=O)nn1-c1ccccc1Cl]

A mixture of 2.94 g (5.0 mmol) of the compound from step a) and 30 mg (0.27 mmol) of caesium carbonate in 52 ml of methanol was stirred at RT overnight. The reaction mixture was concentrated. The residue was dissolved with ethyl acetate, and washed with 1 N hydrochloric acid solution and then with saturated aqueous sodium chloride solution. The organic phase was dried over magnesium sulphate and concentrated under reduced pressure. This gave 2.63 g (96% of theory) of the title compound.

LC-MS (Method 1): $R_t$=0.94 min; MS(ESIpos): m/z=543.0 [M+H]$^+$ $^1$H NMR (DMSO-d$_6$, 400 MHz): δ=7.93-7.42 (m, 8H), 6.90 (d, 1H), 5.50 (br d, 1H), 5.07 (s, 2H), 4.59 (br s, 1H), 4.30 (br d, 1H), 4.13-3.76 (m, 2H), 1.38 (d, 3H)

Measuring Parameters of the X-Ray Diffractometry for the Analysis of the Compound of the Formula (I) in Crystalline Form of Polymorph I:

| Scan axis | gonio |
|---|---|
| Start position [°2θ] | 2.0066 |
| End position [°2θ] | 37.9906 |
| Measurement temperature [° C.] | 25 |
| Anode material | Cu |
| K-alpha1 [Å] | 1.54060 |
| K-alpha2 [Å] | 1.54443 |
| K-beta [Å] | 1.39225 |
| K-alpha 2/K-alpha 1 | 0.50000 |
| Generator setting | 40 mA, 40 kV |
| Incident beam monochromator | focusing x-ray mirror |
| Sample rotation | yes |

TABLE 1

| Peak maxima of the 2 theta angle Peak maximum [2 theta] Polymorph I |
|---|
| 5.6 |
| 7.0 |
| 7.5 |
| 8.9 |
| 9.4 |
| 10.6 |
| 10.8 |
| 13.3 |
| 14.4 |
| 14.7 |
| 15.1 |
| 15.5 |
| 16.8 |
| 17.0 |

TABLE 1-continued

| Peak maxima of the 2 theta angle Peak maximum [2 theta] Polymorph I |
|---|
| 17.7 |
| 17.9 |
| 18.1 |
| 18.4 |
| 18.8 |
| 19.3 |
| 20.3 |
| 20.9 |
| 21.1 |
| 21.2 |
| 21.6 |
| 21.8 |
| 22.1 |
| 22.4 |
| 23.0 |
| 23.2 |
| 23.4 |
| 23.7 |
| 24.0 |
| 24.1 |
| 24.6 |
| 25.0 |
| 26.1 |
| 27.1 |

DESCRIPTION OF THE FIGURES

The figure illustrates X-ray diffractogram of the compound of the formula (I-A-1) in crystalline form of polymorph I.

The invention claimed is:
1. A process comprising steps [C] reacting a compound of the general formula (XI),

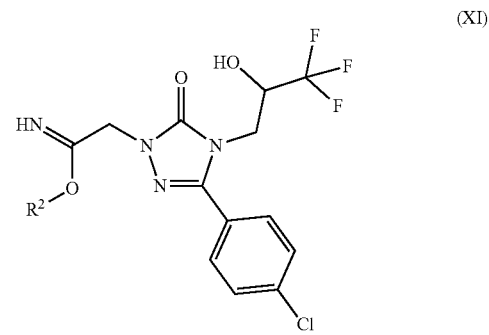

wherein R$^2$ is (C$_1$-C$_4$)-alkyl,
in a first step [C-1] in the presence of a base, with an acid chloride of the general formula (XII)

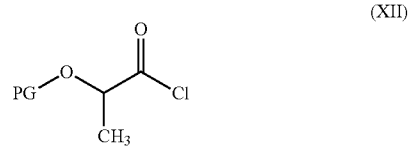

wherein
PG is a protecting group,
and reacting the resultant intermediate in a second step [C-2] in the presence of a base, with a phenylhydrazine compound of the general formula (XIII)

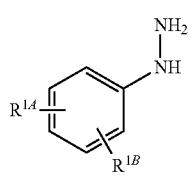

(XIII)

where $R^{1A}$ and $R^{1B}$ are independently selected from the group consisting of hydrogen, fluorine, chlorine, methyl, monofluoromethyl, difluoromethyl, trifluoromethyl, ethyl, methoxy, difluoromethoxy and trifluoromethoxy to produce a 1,2,4-triazolyl compound of the general formula (XIV)

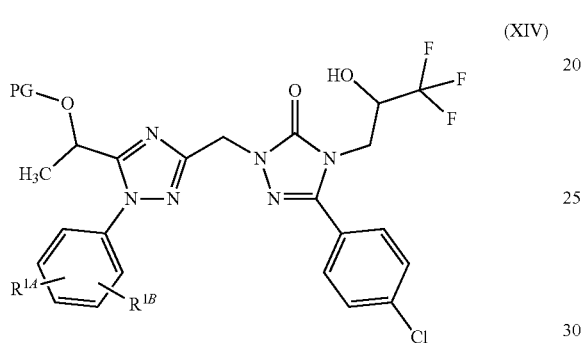

(XIV)

wherein PG is a protecting group, and $R^{1A}$ and $R^{1B}$ have the same definitions as for compound XIII, and reacting compound XIV in a third step [D] by detachment of the protecting group PG to produce a compound of the general formula (I)

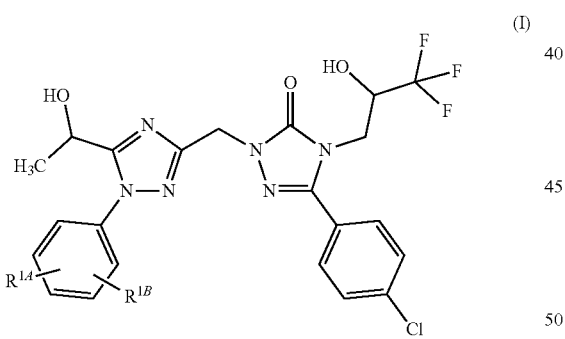

(I)

where $R^{1A}$ and $R^{1B}$ have the same definitions as for compound XIII.

2. The process according to claim 1, wherein the process is conducted as a one-pot reaction in the presence of a suitable solvent and the intermediate that results from step [C-1] is then converted without isolation , in step [C-2].

3. The process according to claim 1, wherein the process is conducted as a one-pot reaction in the presence of a solvent and the 1,2,4-triazolyl compound of the general formula (XIV) obtained from step [C-2] is converted without isolation in a step [D] to a compound of the general formula (I).

4. The process according to claim 1, wherein $R^{1A}$ and $R^{1B}$ are independently selected from the group consisting of hydrogen, fluorine and chlorine, and wherein at least one of the substituents is not hydrogen.

5. The process according to claim 1, which comprises, prior to step [C], a step [B], wherein in step [B] a compound of formula (X)

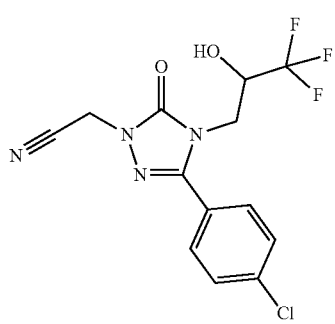

(X)

is reacted with a basic $(C_1-C_4)$-alkoxylate, to give an imino ester compound of formula (XI)

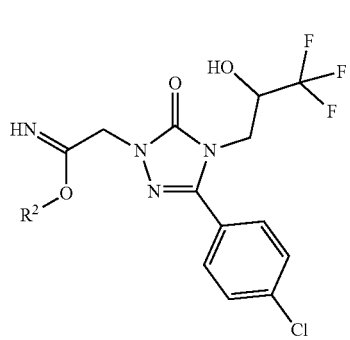

(XI)

wherein
$R^2$ is $(C_1-C_4)$-alkyl.

6. The process according to claim 5, wherein the process is conducted as a one-pot reaction in the presence of a solvent and the imino ester compound of the general formula (XI) that results from step [B] is then converted without isolation in a step [C].

7. The process according to claim 5, wherein the process comprises, prior to step [B], a step [A], wherein in step [A] a compound of formula (II)

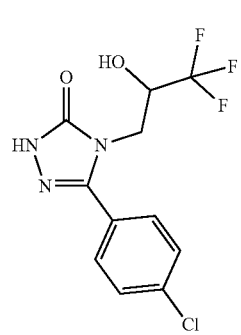

(II)

is reacted with a nitrile compound (IX)

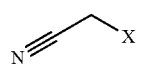

(IX)

wherein X is a leaving group, to produce a compound of formula (X)
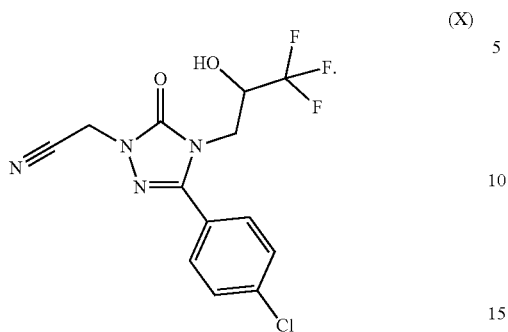
8. The process of claim 1, wherein
$R^2$ is methyl; or
PG is acetyl.
9. The process of claim 5, wherein the basic $(C_1-C_4)$-alkoxylate is sodium methoxide; or
$R^2$ is methyl.
10. The process of claim 7, wherein X is chloride or bromide.
* * * * *